(12) United States Patent
Kang et al.

(10) Patent No.: US 6,835,722 B1
(45) Date of Patent: Dec. 28, 2004

(54) PHARMACEUTICAL COMPOSITIONS AND PREPARATIONS FOR TREATMENT OF METABOLIC BONE DISEASE

(75) Inventors: Sung An Kang, Seoul (KR); Kyung Hee Lee, Anyang (KR); Chung Shil Kwak, Seoul (KR); Chang Jong Kim, Seoul (KR); Yong Oh Lee, Koyang (KR)

(73) Assignee: Yuyu Industrial Co., Ltd. (KR)

( * ) Notice: Subject to any disclaimer, the term of this patent is extended or adjusted under 35 U.S.C. 154(b) by 0 days.

(21) Appl. No.: 10/111,270

(22) PCT Filed: Oct. 20, 2000

(86) PCT No.: PCT/KR00/01188

§ 371 (c)(1),
(2), (4) Date: Apr. 19, 2002

(87) PCT Pub. No.: WO01/28564

PCT Pub. Date: Apr. 26, 2001

(30) Foreign Application Priority Data

Oct. 20, 1999 (KR) ...................................... 1999/456623

(51) Int. Cl.$^7$ .......................... A61K 31/59; A61K 31/66
(52) U.S. Cl. ......................... 514/167; 514/107; 514/108
(58) Field of Search ................................ 514/167, 108, 514/107, 76

(56) References Cited

U.S. PATENT DOCUMENTS 5,431,920 A * 7/1995 Bechard

FOREIGN PATENT DOCUMENTS

| FR | 884628 | 8/1943 |
|---|---|---|
| JP | 07-330613 | 12/1995 |

OTHER PUBLICATIONS

Frediani et al., Effects of combined Treatment with Calcitriol plus Alendronate on Bone Mass and Bone Turnover in Postmenopausal Osteoporosis Two Years of Continuous Treatment, Clin. Drug Invest., Mar. 1998 15 (3) 235–244.*

Gennaro et al., Ed. Remington's Pharmaceutica Sciences, 18$^{th}$ Ed., 1990, pp. 1307–1308, 1634–1644.*

Bruno Frediani, et al., Effects of Combined Treatment With Calcitriol Plus Alendronate on Bone Mass and Bone Turnover in Postmenopausal Osteoporosis Two Years of Continuous Treatment, Clinical Drug Investigation (1998), Mar., 15(3), pp. 235–244.

John F Aloia, M.D., et al., Calcitriol in the Treatment of Postmenopausal Osteoporosis, American Journal of Medicine, vol. 84, Mar. 1988, pp. 401–408.

James D. Fraser, et al., Induction of Matrix GLA Protein Synthesis During Prolonged 1,25–Dihydroxyvitamin $D_3$ Treatment of Osteosarcoma Cells, Calcif Tissue Int. (1990) Apr., 46(4), 270–279.

Dr. Liherman, et al., Effect of Oral Alendronate on Bone Mineral Density and the Incidence of Fractures in Postmenopausal Osteoporosis, The New England Journal of Medicine, (1995), 333, 1437–1443.

* cited by examiner

*Primary Examiner*—Theodore J. Criares
(74) *Attorney, Agent, or Firm*—Lowe Hauptman Gilman & Berner, LLP

(57) ABSTRACT

The present invention relates to a pharmaceutical composition for the treatment of metabolic bone disease and the method of preparation thereof, and more particularly, to an improved pharmaceutical composition for the therapeutic treatment of metabolic disease and the method of preparation thereof, wherein said composition is prepared as a composite pharmaceutical agent which comprises calcitriol; which reduces the rate of spine fractures and increases bone density; alendronate, a bone resorption inhibitor, as two main active ingredients in an optimal mixing ratio to exert the greatest synergistic therapeutic effect; and adequate amount of other additives such as a resorption fortifier of alendronate. Thereof, the pharmaceutical composition according to the present invention can inhibit hypercalcemia caused when administered by calcitriol alone, compensate the inhibitory activity of bone remodeling caused by alendronate due to the presence of calcitriol, and improve drug compliance associated with the usual difficulty in administration as well as a side effect in esophagus, thus effectively preventing the occurence of osteoporosis.

16 Claims, 11 Drawing Sheets

(A)

(B)

(C)

(D)

(E)

(F)

(G)

PHARMACEUTICAL COMPOSITIONS AND PREPARATIONS FOR TREATMENT OF METABOLIC BONE DISEASE

BACKGROUND OF THE INVENTION

1. Field of the Invention

The present invention relates to a composite pharmaceutical composition for the treatment of metabolic bone disease and the method of preparation thereof, wherein said composition is prepared as a composite pharmaceutical agent comprising calcitriol, alendronate, and adequate amount of other additives. The pharmaceutical composition according to the present invention can inhibit hypercalcemia caused when administered with calcitriol alone, compensate the inhibitory activity of bone remodeling caused by alendronate due to the presence of calcitriol, and also improve drug compliance, thus effectively preventing the occurrence of osteoporosis.

2. Description of the Related Arts

Osteoporosis is a systemic metabolic bone disease characterized by a decrease in bone mass as well as a microstructural change in bone without affecting the chemical composition of bone itself which results in increased susceptibility to bone fractures. In particular, senile patients are known to be more vulnerable to bone fractures, which often result from even minor physical shocks; in fact, approximately 1.3 million out of 25 million osteoporosis patients in the U.S. are known to suffer from bone fractures each year, which accounts for almost 10% of total U.S. population.

Osteoporosis can be divided into type I and type II. Type I osteoporosis occurs most frequently in postmenopausal women and is characterized by having a marked increase of bone resorption due to deficiency of estrogen. It is very marked increase of bone resorption due to deficiency of estrogen. It is very common to observe type I osteoporosis patients lose trabecular bone and this causes frequent fractures of spines or wrists. Meanwhile, type II osteoporosis usually occurs in elderly people or in males and is characterized by a drastic decrease in bone remodeling capability rather than an increase in bone resorption. However, the increase in bone resorption as well as the decrease in calcium absorption by osteoclasts are known to be common to both types of osteoporosis.

Therapeutic agents employed in treating osteoporosis in clinical fields are generally divided into two groups; a group that can expedite bone remodeling and another that can prevent bone resorption. The examples of active therapeutic agents that can promote fast bone remodeling include anabolic steroids, fluoride, vitamin D and parathyroid hormones. With the recent introduction of the mechanism of bone formation, vitamin D derivatives have been the object of the public attention because of their roles in mediating balanced bone mass. Calcitriol, being one of the active vitamin $D_3$ derivatives expressed as 1,25-$(OH)_2$ $D_3$, is one of the above-mentioned bone remodeling activators, and is also a hormone which enables to prevent osteoporosis because it can not only increase calcium absorption from the intestinal tract but also can inhibit the decrease of bone mass. However, calcitriol is also shown to cause hypercalcemia when used alone. Hypercalcemia, a metabolic disease characterized by having a plasma calcium concentration of 11.0 mg/dL or above in blood, is one of the most common life-threatening disease closely associated with fatal disease such as a tumor. In fact, calcitriol induces an increase of calcium concentration in blood as well as the abnormal control of calcium concentration by bone metabolism thus resulting in hypercalcemia. The symptoms of hypercalcemia or calcium addiction (a severe case of hypercalcemia with prolonged duration) due to side effects of calcitriol and overdose of vitamin D are very similar to that shown in hypercalcemia. Hypercalcemia occasionally entails acute symptoms such as anorexia, headache, emesis, constipation, and chronic symptoms of hypercalcemnia include dystrophy, paresthesia, pyrexia with thirst, hyperurisis, dehydration, acedia, groweighth retardation, urinary infection, etc. Patients with hypercalcemia often experience to have complications and this adds difficulty in treating disease such as osteoporosis.

The conventional pharmaceutical agents used in treating osteoporosis as bone resorption inhibitors include estrogen, calcitonin, bisphosphonate and ipriflavone.

Japanese Patent Publication No. 7-330613 discloses a bone remodeling activator, which contains alendronate, a kind of bisphosphonates, as an active agent and can activate the calcification of osteoblasts as well as the formation of bone matrix in the presence of dihydroxy vitamin $D_3$.

French Patent Application No. 884628 discloses a pharmaceutical agent for oral administration which uses bisphosphonate as a substrate and contains an adequate amount of sodium lauryl sulfate.

Application Ser. No. 09/125,372 discloses enteric coated tablets that contain bisphosphonates.

However, the above-mentioned bone resorption inhibitors have not been successful in sufficiently improving the bone mass of patients with already progressed osteoporosis and thus there has been along-awaited need for the development of very effective bone remodeling activators.

A recent Italian report discloses a method of combined administration of both alendronate and calcitriol [Clinical Drug Investigation (1998) March, 15(3), 235-244]. In this report, alendronate and calcitriol were not administered as a composite tablet but were administered independently. For example, alendronate was administered once a day while calcitriol was administered twice a day with a certain timely interval allowed between each administration.

Furthermore, the alendronate must be administered before meals because the pharmaceutical effect was shown much decreased due to poor absorption when they were taken after meals.

Considering that most osteoporosis patients are elderly people and that most of them also take various kinds of drugs daily, it appears very plausible that the patients often forget to take one or two drugs that they are supposed to take because of the rather complicated nature of administration of the above drugs and thus the effects of slid administration also remain questionable.

Alendronate can cause a local stimulation on mucous membranes at the upper gastrointestinal tract and this often results in a few side effects in esophagus such as esophagitis, esophageal ulcer, esophageal erosion. Therefore, it becomes necessary for patients to take in sufficient amount of water when they take a drug containing alendronate so that the drug they are taking can pass through the esophagus as promptly as possible and thus keeping esophageal stimulation to the minimal level. And his has been also raised as a burden to most patients that lowers drug compliance.

In the Conference of Japanese and American Glaucoma Societies' held in Vancouver, Canada in January 1997, it was announced that the final goal of developing composite pharmaceutical agents was to improve drug compliance. In the 'Fifth Conference on Retroviruses and opportunistic infection' which was held in Chicago on Feb. 4, 1998, it was shown that the effect of Combivir, a composite pharmaceutical agent containing both lamivudine and zidovudine wherein the pharmaceutical mechanisms differ from each other, had an improved therapeutic effect of 96% as compared to 72% of effect obtained when lamivudine and zidovudine were administered independently as a separate drug, respectively, and here the improvement in therapeutic effect is speculated to be due to the improvement in drug compliance of the patient to the composite pharmaceutical agent.

There have been no studies conducted on the therapeutic treatment of osteoporosis with respect to preparation of composite tablets containing both calcitriol and alendronate, and instead there have been many lines of studies focused on the effect of alendronate as a therapeutic agent treating hypercalcemia caused by vitamin D intake. Therefore, it is in high demand to develop composite pharmaceutical agents with advanced formulation technologies for the treatment of osteoporosis which can not only minimize side effects such as hypercalcemia, caused when calcitriol was administered alone, but can prevent/treat osteoporosis with a little dose and enhance drug compliance, which is usually low in conventional drugs, by remedying the rather complicated way of administration and preventing esophageal side effects.

SUMMARY OF THE INVENTION

The present invention relates to a pharmaceutical composition for the treatment of metabolic disease and the method of preparation thereof, and more particularly, to an improved pharmaceutical composition for the therapeutic treatment of metabolic disease and the method of preparation thereof, wherein said composition is prepared as a composite pharmaceutical agent comprising (a) calcitriol; which reduces the rate of spine fractures and increases bone density; (b) alendronate, a bone resorption inhibitor, as active ingredients in an optimal mixing ratio to exert the greatest therapeutic effect; and (c) adequate amount of additives such as resorption fortifier of alendronate, so that the resulting composition can reduce hypercalceria caused by calcitriol, compensate the inhibitory activity of bone remodeling caused by alendronate due to calcitriol, improve drug compliance usually accompanied because of the difficulty in administration and the usual side effects in esophagus, thus effectively preventing the occurrence of osteoporosis.

For the FIGS. 1–7, A–F represent groups of experimental Sprague-Dawley white rats treated as shown below.

A: No Treatment
B: Single Treatment with Excipients
C: Single Treatment with Calcitriol (0.1 $\mu$g/kg)
D: Single Treatment with Alendronate (1.0 mg/kg)
E: Composite Treatment 1 [Calcitriol (0.1 $\mu$g/kg)+ Alendronate (0.5 mg/kg)]
F: Composite Treatment 2 [Calcitriol (0.1 $\mu$g/kg)+ Alendronate (1.0 mg/kg)]
G: Composite Treatment 3 [Calcitriol (0.1 $\mu$g/kg)+ Alendronate (2.0 mg/kg)]

Figure 8:
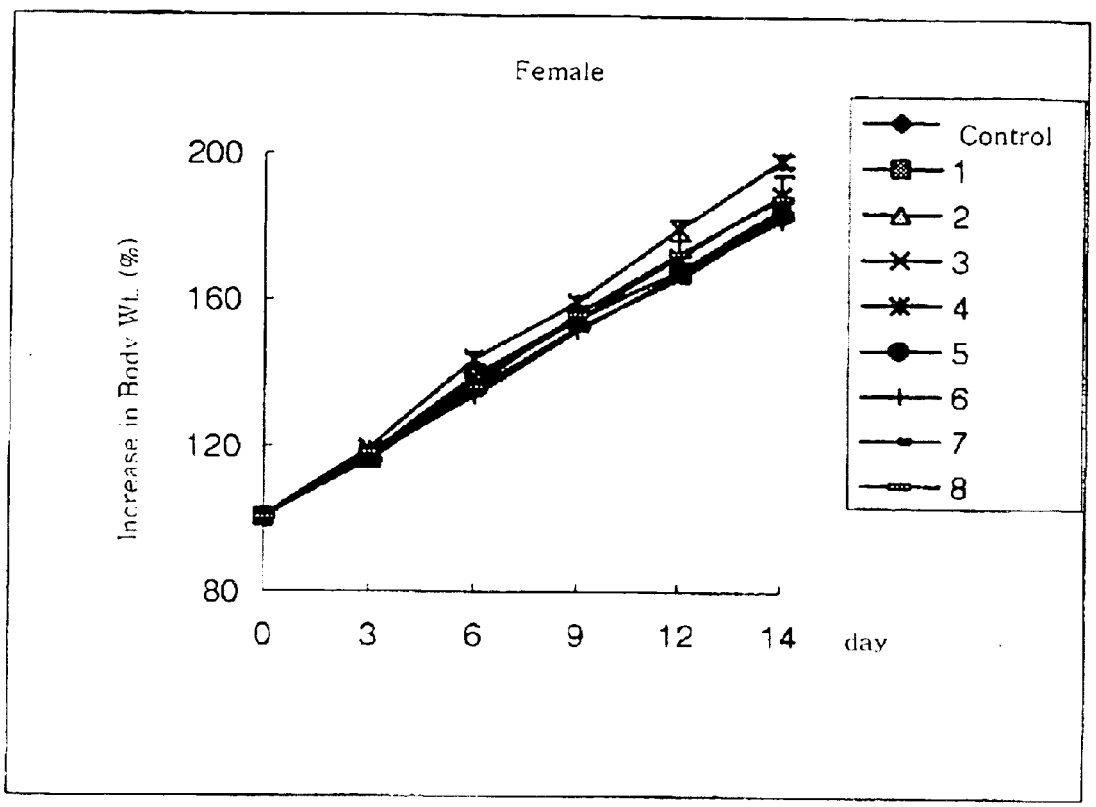
Figure 8:
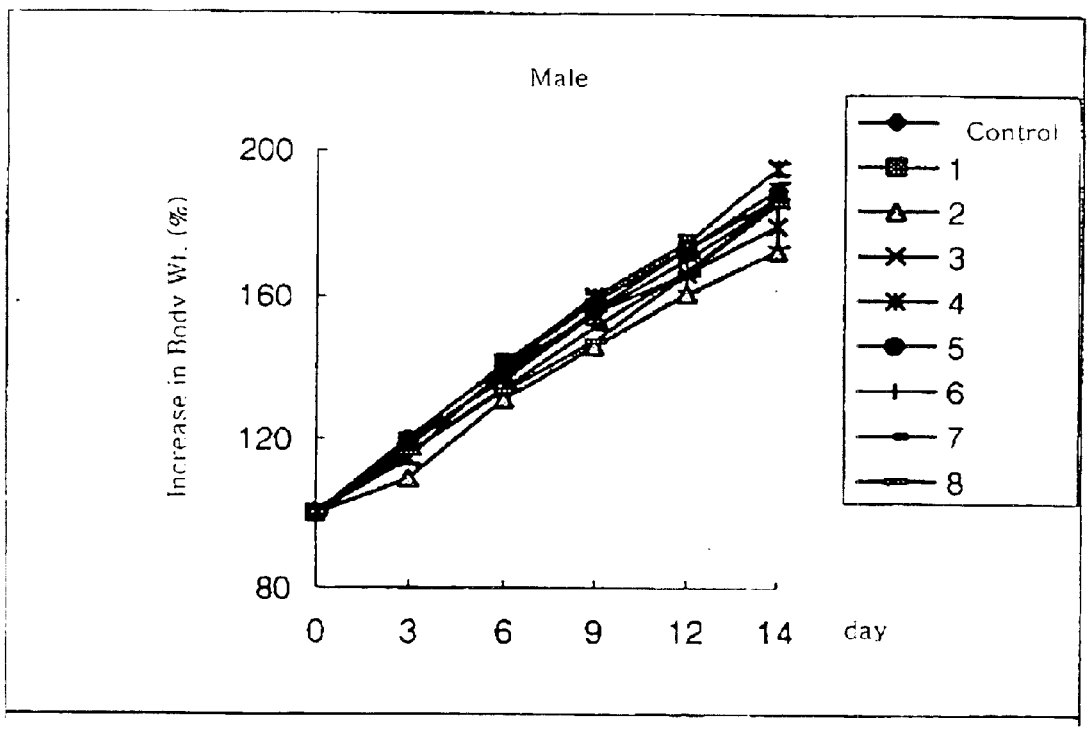

FIG. 8 is a graph that shows the change in body weight of Sprague-Dawley white rats observed for 2 weeks which were orally treated with a composite pharmaceutical agent containing both calcitriol and alendronate.

Figure 9:
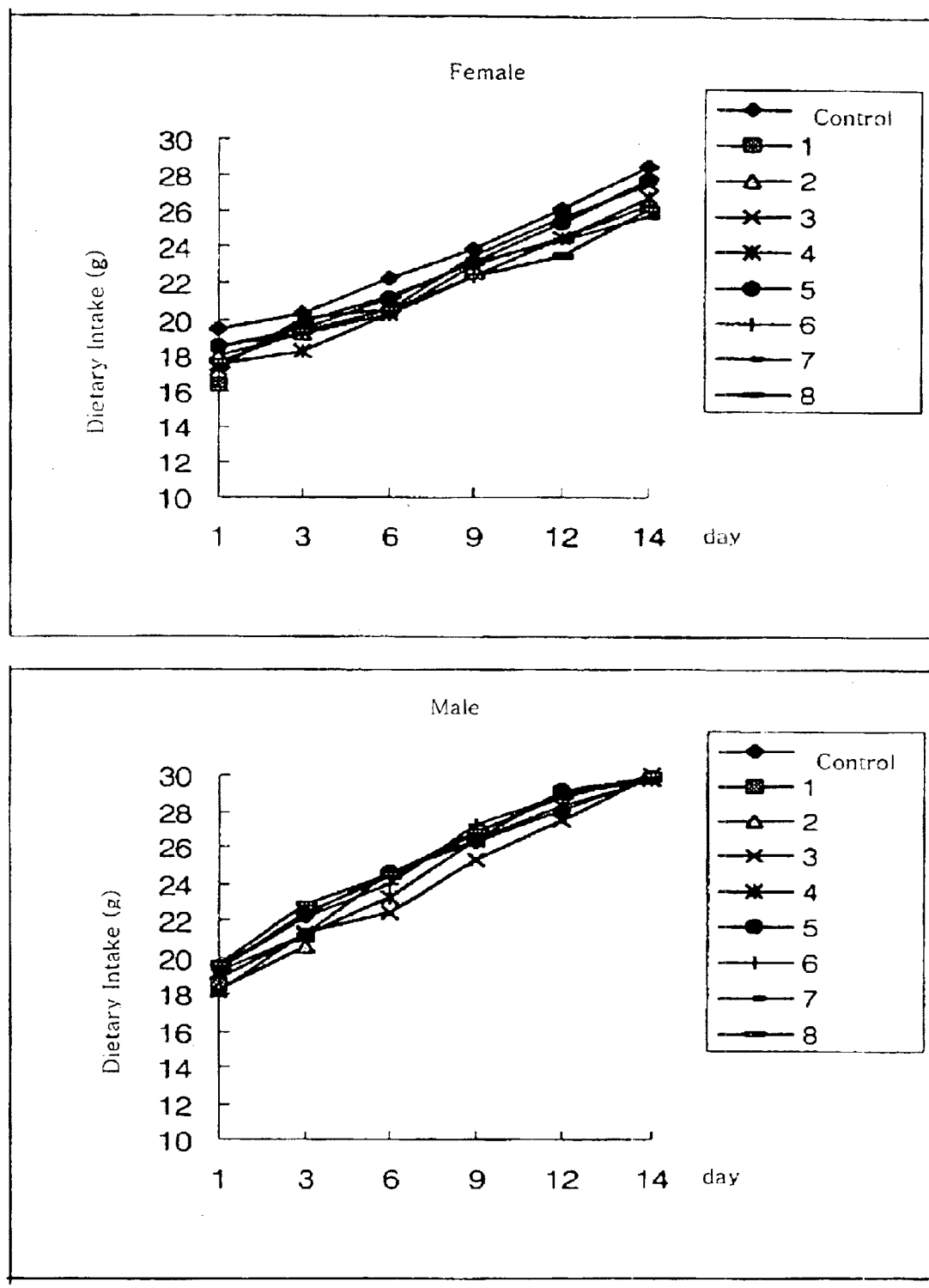

FIG. 9 is a graph that shows the dietary intake of Sprague-Dawley white rats observed for 2 weeks, which were orally treated with a composite pharmaceutical agent containing both calcitriol and alendronate.

For the FIGS. 8–9, 1–8 represent groups of experimental Sprague-Dawley white rats treated as shown below.
1: Calcitriol (125 $\mu$g/kg)+Alendronate (1250 mg/kg)
2: Calcitriol (100 $\mu$g/kg)+Alendronate (1000 mg/kg)
3: Calcitriol (75 $\mu$g/kg)+Alendronate (700 mg/kg)
4: Calcitriol (50 $\mu$g/kg)+Alendronate (500 mg/kg)
5: Calcitriol (25 $\mu$g/kg)+Alendronate (250 mg/kg)
6: Calcitriol (5 $\mu$g/kg)+Alendronate (50 mg/kg)
7: Calcitriol (1 $\mu$g/kg)+Alendronate (10 mg/kg)
8: Calcitriol (0.2 $\mu$g/kg)+Alendronate (2.0 mg/kg)

Figure 10:
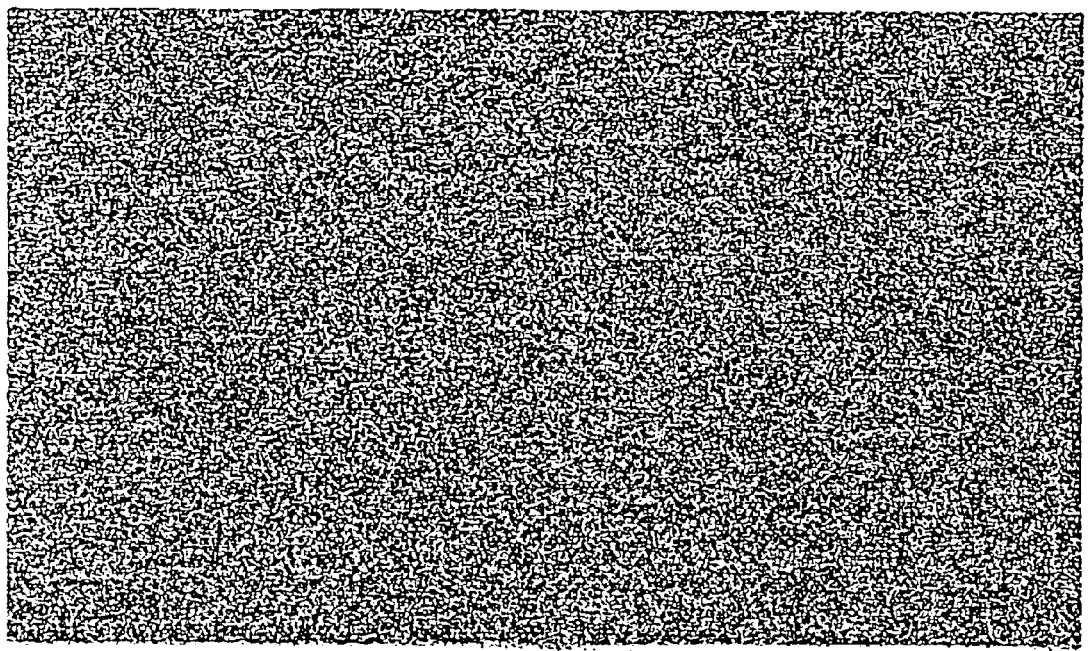

FIG. 10 is a microscopic view (H & E×100) that shows the result of tissue findings of the spleen of Sprague-Dawley white rats orally treated with a composite pharmaceutical agent containing 100 $\mu$g/kg of calcitriol and 1000 mg/kg of alendronate.

Figure 11:
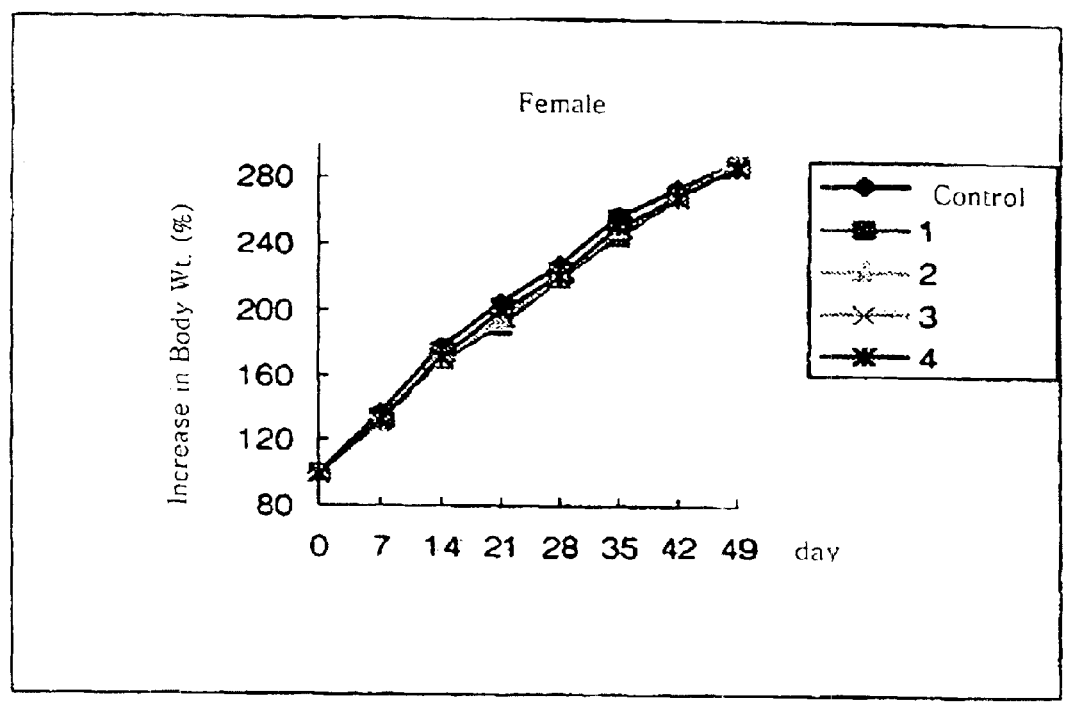
Figure 11:
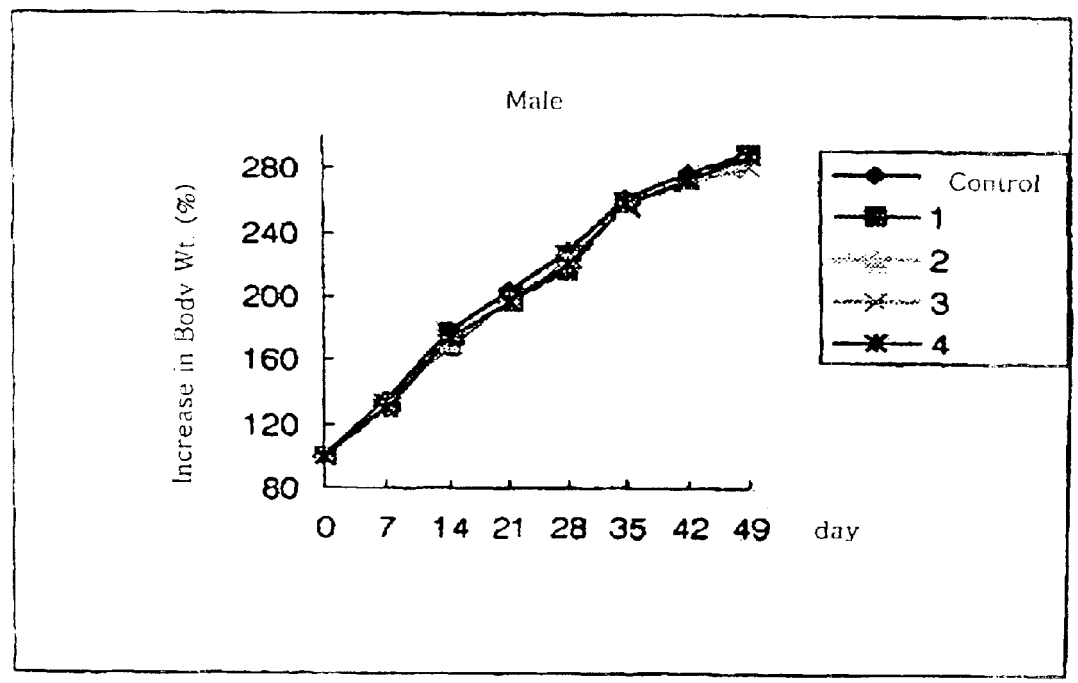

FIG. 11 is a graph that shows the change in body weight of Sprague-Dawley white rats observed for 7 weeks, which were orally treated with a composite pharmaceutical agent containing both calcitriol and alendronate.

Figure 12:
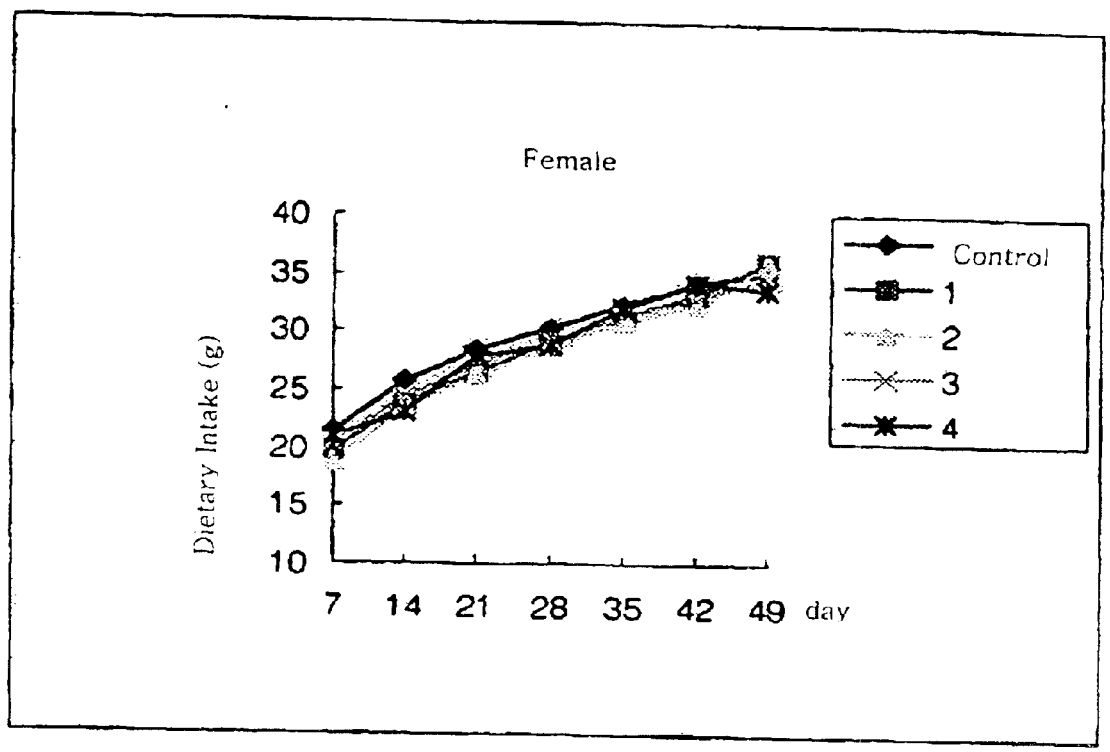
Figure 12:
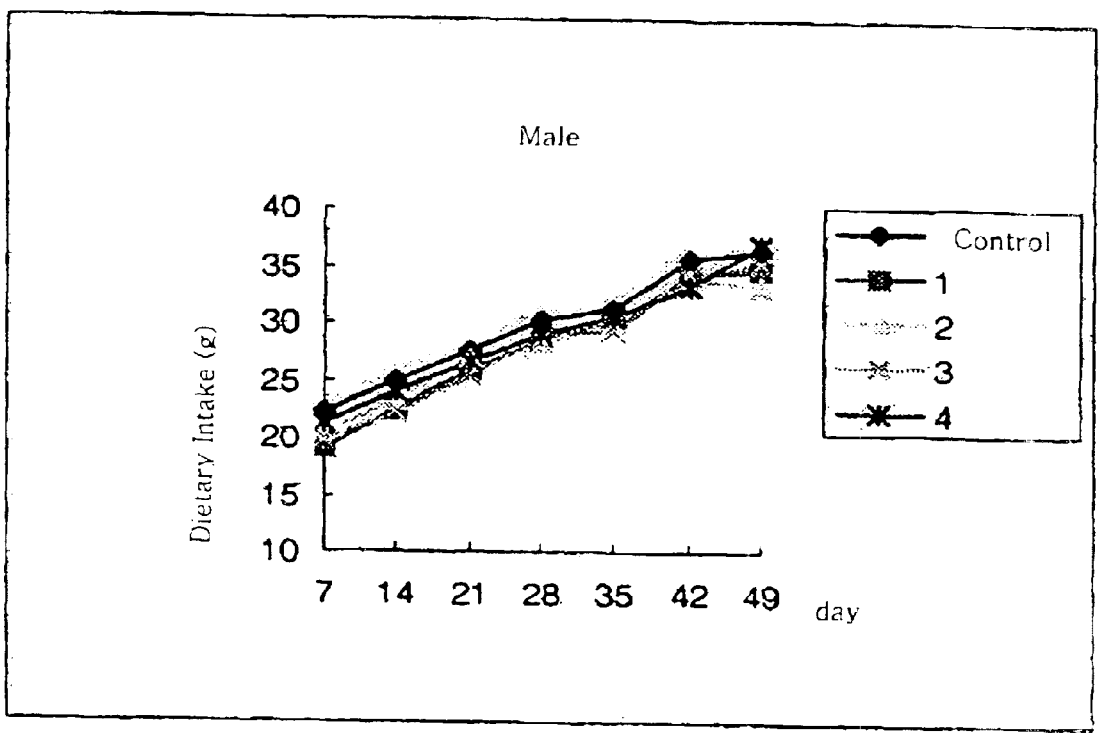

FIG. 12 is a graph that shows the dietary intake of Sprague-Dawley white rats observed for 7 weeks, which were orally treated with a composite pharmaceutical agent containing both calcitriol and alendronate.

For the FIGS. 11–12, 1–4 represent groups of experimental Sprague-Dawley white rats medicated as shown below.
1: Calcitriol (25 $\mu$g/kg)+Alendronate (250 mg/kg)
2: Calcitriol (5 $\mu$g/kg)+Alendronate (50 mg/kg)
3: Calcitriol (1 $\mu$g/kg)+Alendronate (10 mg/kg)
4: Calcitriol (0.2 $\mu$g/kg)+Alendronate (2 mg/kg)

DETAILED DESCRIPTION OF THE INVENTION

The present invention relates to a pharmaceutical composition for the treatment of metabolic bone disease characterized by having calcitriol and alendronate as two active ingredients wherein said pharmaceutical composition contains 1,000 to 50,000 parts by weight of alendronate per 1 part by weight of calcitriol.

The present invention also relates to a process of preparing said pharmaceutical composition containing calcitriol and alendronate as active agents comprising a) a process of obtaining calcitriol granules;
   by adding mannitol to a mixture of calcitriol and ethanol, subsequent adding ethanol, antioxidant and binder to said mixture,
   pulverizing said mixture into 14–35 mesh size and drying said pulverized mixture;
b) a process of obtaining alendronate granules;
   by mixing mannitol, resorption fortifier and alendronate, subsequently adding ethanol and binder to said mixture,
   pulverizing said mixture into 14–35 mesh size and drying said pulverized mixture;
c) a process of preparing tablets;
   by mixing said calcitriol granules obtained from said step a) and said alendronate granules obtained from said step b) with 1:1 part by weight of mixing ratio followed by subsequent adding of a disintegrating agent and a lubricant to said mixture and tableting the mixture.

This invention is explained in more detail by the following examples, but they should not be construed as limiting the scope of this invention.

The present invention relates to a method of manufacturing a composite pharmaceutical agent comprising calcitriol and alendronate as its two active ingredients at its optimal mixing ratio, wherein the former ingredient is known to be effective in reducing spinal fractures and increasing bone density while the latter effective in inhibiting bone resorption, followed by the addition of resorption fortifier.

The above two active ingredients are further elucidated as follows.

First, calcitriol expressed as $1,25\text{-}(OH)_2\text{-}D_3$, is one of active vitamin $D_3$ derivatives involved in calcium transport in intestinal tract and is already known that it can activate intestinal calcium absorption as well as it can reduce the secretion of parathyroid hormone thus alleviating the bone loss of menopausal women suffering from osteoporosis [Aloia J. F., *Am J Med* (1988), 84, 401–8]. In addition, calcitriol is also known to activate the production of osteocalcin, a bone-specific protein involved in mineralization of bones with respect to osteoblats [Price P. A., *Calcif Tissue Int* (1990) Apr., 46(4), 270–9]. However, calcitriol as a pharmaceutical agent also has a problem because it can often cause hypercalcemia when administered alone and therefore there have been many lines of studies in order to resolve this drawback.

Second, alendronate, expressed as 4-amino-hydroxybutylidine-1,1-bisphosphonate, is a kind of bisphosphonates developed as a therapeutic agent for the treatment of osteoporosis and is known to prevent bone loss by inhibiting the activity of osteoclasts thus helping to improve the bone density. In fact, clinical studies showed that there was about 2–3% increase in bone density. For example, a clinical study which was implemented on 994 post-menopausal women from 16 different countries showed that there was a gradual increase in mineral density of spinal bone and bones of lower limbs. Also, the rate of occurrence of new spinal fracture in a group medicated with alendronate was reduced by about 48% as compared to that of a placebo group.

In general, the mineral density of a bone is closely associated with bone density and thus the rate of occurrence of bone fracture becomes drastically decreased as the mineral density becomes higher. When alendronate was administered 10 mg/day for 3 years (10 mg/day of alendronate is thought to have the most effective therapeutic effect [Liberman, *N. Engl. J. Med.* (1995), 333, 1437–1443], the mineral densities of spinal bone and bones of lower limbs were increased by 8.2% and 7.2%, respectively, whereas the mineral density on a placebo group was dropped by 0.7% during the same period of administration. However, alendronate is shown to adversely affect the normal cycles of bone metabolism by reducing the rate of bone remodeling and is therefore a composite pharmaceutical agent necessitated to compensate this problem.

Since alendronate is able to prevent hypercalcemia, which is known as the most serious side effect caused by calcitriol, it has been postulated that combined administration of both alendronate and calcitriol would be able to resolve hypercalcemia and also enable to administer optimal amount of calcitriol, which has been limited its daily dosage due to its narrow safety margin. Moreover, the antagonistic activity of alendronate against bone remodeling will be also compensated by the presence of calcitriol.

As a way to develop a most effective composite pharmaceutical agent for the treatment of post-menopausal women, experimental animals were first induced to develop osteoporosis in the present invention and then they were placed under numerous experiments of administering various concentrations of mixtures of calcitriol and alendronate resulted from various mixing ratios between calcitriol and alendronate, and finalized their optimal mixing ratio which can not only effectively prevent osteoporosis without retarding the rate of bone remodeling but also can control the calcium concentration in blood to be kept at normal level. The results showed that the optimal concentration ratio between the two ingredients of a pharmaceutical agent was to contain 1,000–50,000 parts by weight of alendronate with respect to 1 part by weight of calcitriol. If the amount of alendronate contained in said pharmaceutical agent is less than 1,000 parts by weight per 1 part by weight of calcitriol, the resulting plasma calcium concentration will be increased and there will be a high risk of causing hypercalcemia when administered with the pharmaceutical agent. On the other hand, the amount of alendronate contained in said pharmaceutical agent is more than 50,000 parts by weight per 1 part by weight of calcitriol, it will adversely affect the normal cycles of bone metabolism by reducing the rate of bone remodeling.

The pharmaceutical agents according to the present invention can be prepared in various dosage forms such as naked tablets, enteric coated tablets, granules, enteric coated granules, capsules, and enteric coated capsules. Further, it is recommended to use each ingredient being in the range of 0.1–5.0 μg for calcitriol and 1–50 mg for alendronate per each dosage unit.

Additives were selected after a series of experiments from those which have been already shown their effectiveness in preparing pharmaceutical agents. Adequate amount of selected additives were then added to each of the above two active ingredients respectively to prepare two preliminary preparations and then they were combined together to finally form a composite pharmaceutical agent. Thus obtained composite pharmaceutical agent exhibited much improved drug compliance compared to those of conventional pharmaceutical drugs which have relatively low drug compliance mainly due to the difficulty in administration and the side effects in esophagus, thus effectively preventing the osteoporosis.

The specific features of the manufacturing processes employed in the present invention are as follows.

Process A

In the present invention, mannitol is added to a mixture of calcitriol and ethanol and then mixed, and then ethanol, an antioxidant and a binder are added to the mixture and mixed.

The resulting mixture is then pulverized into a size of 14–35 mesh and then dried at 30–50° C. to generate calcitriol granules. Here, if the size of the mixture is less than 14 mesh then the resulting calcitriol granules become non-homogeneous while if the size is larger than 35 mesh the production yield becomes low and the processability in tableting also becomes worsened.

Process B

In a separate step apart from the above process A, alendronate, mannitol and an resorption fortifier are mixed together, and then added with ethanol and a binder.

The resulting mixture is then pulverized into a size of 1435 mesh and then dried at 30–50° C. to generate alendronate granules. Here, if the size of the mixture is less than 14 mesh then the resulting alendronate granules become non-homogeneous while if the size is larger than 35 the production yield becomes low and the processability in tableting also becomes worsened.

Process C

The calcitriol granules and alendronate granules obtained from the above mentioned process A and B, respectively, are mixed together, added with a disintegrating agent and a lubricant, and the resulting mixture is tableted to finally produce the composite pharmaceutical agent of the present invention.

The additives used in the present invention are described hereunder.

First, mannitol is used as an excipient in the above processes A and B, and the amount of mannitol used in the processes A and B is limited so that the amount be 50–60 weight % and 40–60 weight % of the total amount of mannitol contained in the final pharmaceutical composition, respectively.

The reasons of limiting the amount of mannitol are as follows. The miscibility test between calcitriol and alendronate showed that the mixture of the two components resulted in deterioration of the stability of calcitriol. However, in a compatibility test, when calcitriol was mixed with other excipients before mixing with alendronate the calcitriol in the resulting mixture remained stable. Therefore, in order to avoid the direct contact between calcitriol and alendronate, the inventors of the present invention first diluted calcitriol and alendronate independently with mannitol to produce their granules and then mixed them thereafter. With respect to the amount of mannitol used in preparing said granules, it was found that the amount of mannitol is important in maintaining homogeneity of said granules.

When both granules of calcitriol and alendronate were prepared by using 50% of the total mannitol, respectively, there were observed differences in the resulting granules in terms of specific volume and the tablets subsequently obtained after mixing and tableting of said granules were not uniform in the amount of said ingredients. Therefore, numerous experiments were conducted to find an optimal amount of mannitol to produce a homogeneous granule as well as to contain an equal amount of each given ingredient; as a result, it was found that using about 50–60% of total mannitol is suitable for the preparation of calcitriol granules, and preferably 52%, while about 40–60% of total mannitol is recommended for the preparation of alendronate granules, and preferably 48%. The above two granules were then adjusted to have equal amount before mixing them together.

The examples of excipients that can be used in the present invention include white sugar, cellulose and lactose as well as mannitol, and preferably D-mannitol. These excipients are recommended to use 10–98 weight %, and preferably 7097 weight %. If the amount of mannitol added is off the above range then the processability in tableting becomes worsened.

Antioxidants that can be used in the present invention are one or more selected from the group consisting of butylated hydroxytoluene(BHT), (butylated hydroxyanisole(BHA), DL-alpha-tocopherol and lecithin, and preferably butylated hydroxytoluene(BHT) and butylated hydroxyanisole(BHA). These antioxidants can be used 0.001–10 weight % of the total pharmaceutical composition, and preferably 0.01–1.0 weight %. If the amount of antioxidants is off the above range then there will be raised a problem of calcitriol stability.

A binder can be selected from the group consisting of pyrrolidone, hydroxypropyl methyl cellulose, hydroxypropyl cellulose and carboxy methylcellulose sodium.

The recommended amount of the binder as an additive is to use 0.1–20 weight % of the total pharmaceutical composition, and preferably 1–10 weight %. If the amount of a binder is off the above range then the processability in tableting will be deteriorated due to non-uniform granular distribution.

A disintegrating agent can be selected from the group consisting of croscarmellose sodium, low-substituted hydroxypropyl cellulose and carboxy methylcellulose calcium, and the recommended amount of the disintegrating agent as an additive is to use 0.1–20 weight % of the total pharmaceutical composition, and preferably 1–10 weight %. If the amount of a disintegrator is off the above range then there will be a problem in the disintegration of tablets.

Examples of lubricants include calcium stearate, magnesium stearate and talc, it is recommended to use 0.1–20 weight % of the total pharmaceutical composition, and preferably 1–10 weight %. If the amount of a disintegrating agent is off the above range then there will be a problem in processability of tableting as well as in the assay of active ingredients.

Sodium lauryl sulfate can be used as a resorption fortifier and its recommended amount of use is 0.01–10 weight % of the total pharmaceutical composition, and preferably 0.1–1 weight %.

In addition, additives for a sustained release can be selected from the group consisting of hydroxypropyl methyl cellulose, methyl cellulose, hydroxypropyl cellulose and ethyl cellulose.

The pharmaceutical components according to the present invention can be prepared as enteric coated tablets by coating with an enteric coating solution and they can be also prepared as capsules by filing a given pharmaceutical composition into conventional type of capsules. The enteric coating solution consists of an enteric coating agent, a plasticizer and a solvent. Examples of the enteric agents are hydroxypropyl methyl cellulose phhalate, metacrylic acid polymer and cellulose acetate phthalate, and examples of platicizers include triethyl citrate, polyethylene glycol and propylene glycol. Solvents used in the present invention are two or more selected from the group consisting of methylene chloride, ethanol, acetone and distilled water.

Thus prepared pharmaceutical agents have shown superior therapeutic effects in treating metabolic bone disease such as osteoporosis, Paget's disease, rachitis, osteomalacia, renal osteodystrophy of renal failure patients, hypoparathyroidism and hyperparathyroidism.

This invention is further illustrated by the following examples. However, these examples should not be construed as limiting the scope of this invention in any manner.

REFERENTIAL EXAMPLE

Optimal concentration ratio was calculated as follows by which not only the progress of osteoporosis can be effectively prevented but the plasma calcium concentration as well as the amount of calcium excretion via urine can be maintained at a normal level while not inhibiting the rate of bone remodeling.

1) Induction of Osteoporosis

Twelve week old matured female Sprague-Dawley white rats were supplied from Daehan Biolink Co., Ltd. (Seoul, Korea) and raised in a clean room of an animal experiment laboratory in a medical school of Seoul National University. The white rats were given a week to adapt by feeding them with normal feedstuff (Purina, chow diet) and then they were divided into 6 different groups wherein each group consisted of 10 white rats with similar weight distribution, and ovariostereses were performed to all of them. The white rats were allowed to freely drink water and have food under a standardized condition of 22° C., 50% humidity, 12 h dark/light cycle.

2) Medication

After the ovariostereses, the white rats were rested for 2 days and then orally administered in the morning for 5 days per week for the duration of 2 months with a medication which contains certain amount of either single or combination of both calcitriol and alendronate, which were independently dissolved in 0.5 mL of purified palm oil and physiological saline, respectively. The amount of medication administered in each group is shown in the following table 1 and the control group was administered only with equal amount of palm oil and physiological saline used in the experimental groups.

TABLE 1

| Classification | | Calcitriol ($\mu$g/kg) | Alendronate (mg/kg) | Purified Palm oil (mL) | Physiological saline (mL) |
| --- | --- | --- | --- | --- | --- |
| Control Group | | — | — | 0.5 | 0.5 |
| Group administered with calcitriol | | 0.1 | — | 0.5 | 0.5 |
| Group administered with alendronate | | — | 1.0 | 0.5 | 0.5 |
| Group administered with both calcitriol and alendronate | 1 | 0.1 | 0.5 | 0.5 | 0.5 |
| | 2 | 0.1 | 1.0 | 0.5 | 0.5 |
| | 3 | 0.1 | 2.0 | 0.5 | 0.5 |

3) Collecting Samples and Pretreatment

After 2 months of the onset of the above medications, 24 h urine samples were collected from the white rats by using a metabolic cage, centrifuged and then stored at −70° C. The white rats under experiment were fasted overnight decapitated, and their blood samples were collected. White rats sera were then obtained by centrifuging those blood samples and were stored at −70° C. Tibiae were separated by ablation and fixed with 4% formalin at pH 7.4.

4) Statistic Data and the Evaluation

The result of each experiment was represented by mean value±standard deviation, and the significance was determined by using ANOVA, Duncan multiple range test at the level of P<0.05.

Experimental Example 1

Bone Histomorphometry

For the decalcification of tibiae fixed on the above referential example, each tibia was placed in a 10% nitric acid solution for 6 h and then dehydrated by passing through 10 different alcohol concentrations ranging from 80% to 100%. Then, it was embedded twice in xylene and paraffin, respectively, cut proximal tibia using a bone-cutting microsaw into 4 cm thick pieces and dyed with hematoxyleneasin. The above proximal tibiae were observed under 42× magnification of a microscope and the ratio between the area of trabecular bone within a standard area of $\mu m^2$ and the standard area was calculated after measuring the area of trabecula by using quantitative image analysis System. The results of bone histomorphometry are as follows.

About 2–3% of cortical bone in humans is replaced annually; in contrast, trabecelar bone is replaced by a much faster rate of 25% per year and thus the rate of development of trabecular bone can be used as a direct as well as an exact W of discerning the state of bone health, and it thus has been widely used in animal experiments. In the present experiment, alendronate and calcitriol were administered either singly or in combination for 2 months after an ovariosteresis and microscopic observation of the trabecular bone of tibia showed that the area of trabecular bone was much reduced as compared to that in a normal group (see FIG. 1). Observations of the experimental groups using the image analyzer revealed that the area of trabecular bone was drastically increased in a group treated with alendronate alone; groups 1, 2 and 3, which were treated with a composite drug, whereas it was not increased in a group medicated with calcitriol alone (see FIG. 2). For example, in terms of the area of trabecular bone, the group treated with a composite drug containing alendronate and calcitriol showed the same effect as in the group treated with alendronate alone, and also there was no difference among the groups 1, 2 and 3, which were treated with a composite medication, respectively.

Experimental Example 2

Biochemical Test

Reagents used were those obtained from the referential example above.

1) Measurement of Serum Calcium Concentration

The serum calcium concentration was measured by using Technicon autoanalyzer and the result is shown below.

There was a significant increase in serum calcium concentration in the group treated with calcitriol alone while the group treated with alendronate alone showed a significant decrease in serum calcium concentration. This is because calcitriol increases calcium absorption in intestine while alendronate inhibits bone resorption by reducing parathyroid hormone, which then prevents the release of calcium from a bone into a blood stream and inhibits the synthesis of calcitriol [1,25-$(OH)_2$-$D_3$] in kidney thus decreasing the calcium absorption in intestine. Therefore, the serum calcium concentrations in groups 1, 2 and 3 administered with a composite drug were maintained at the intermediate levels in between the concentration of the group treated with calcitriol alone and that of the group treated with alendronate alone, as expected (see FIG. 3).

2) Measurement of Calcium Excretion in Urine

Figure 1:
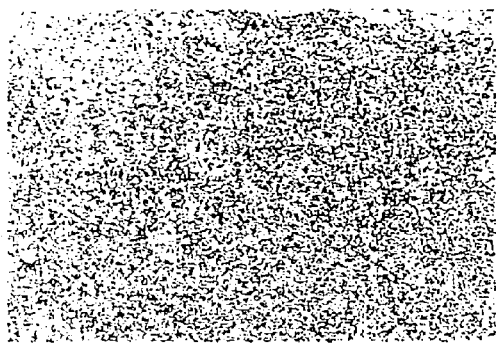
FIG. 1 shows microsopic views (×40) of trabeculae bone of tibia after two months of administration of alendronate and calcitriol, administered either independently or as a concomitant administration of both ingredients, following ovariosteresis.
Figure 1:
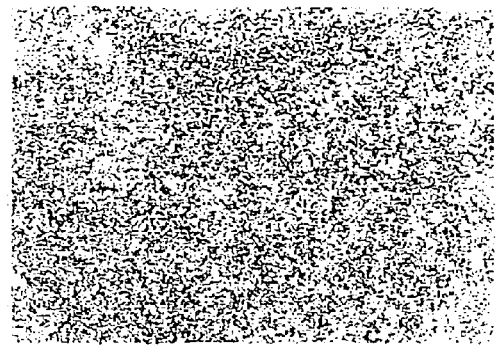
Figure 1:
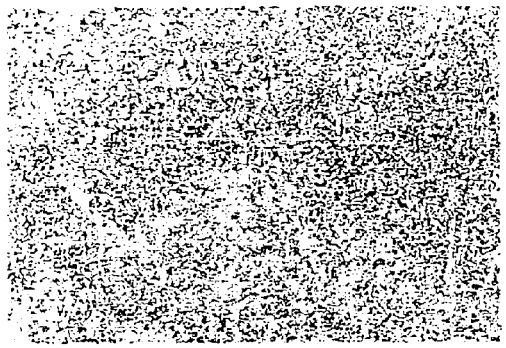
Figure 1:
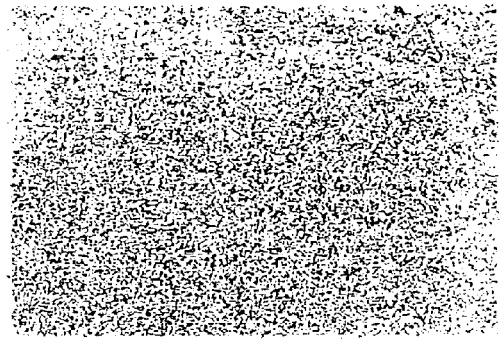
Figure 1:
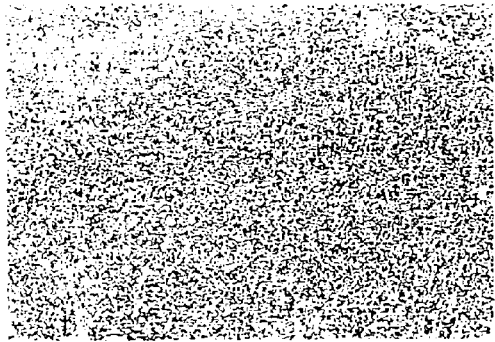
Figure 1:
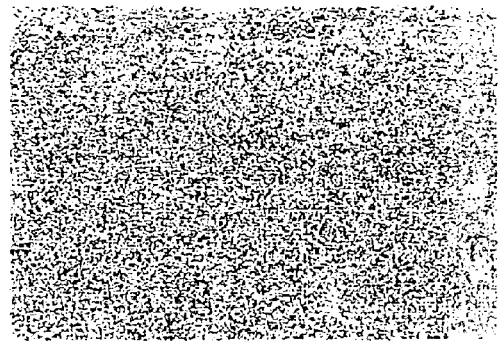
Figure 1:
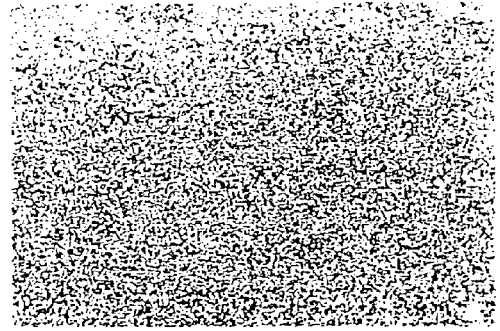
Figure 2:
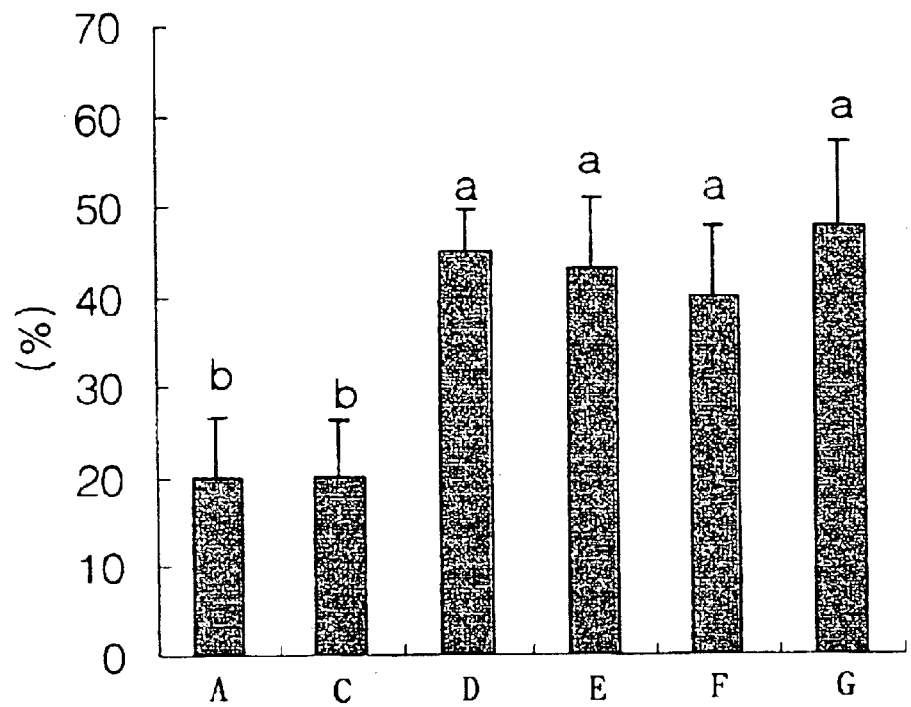
FIG. 2 is a graph that shows the area of trabecular bone observed by using an image analyzer.
Figure 3:
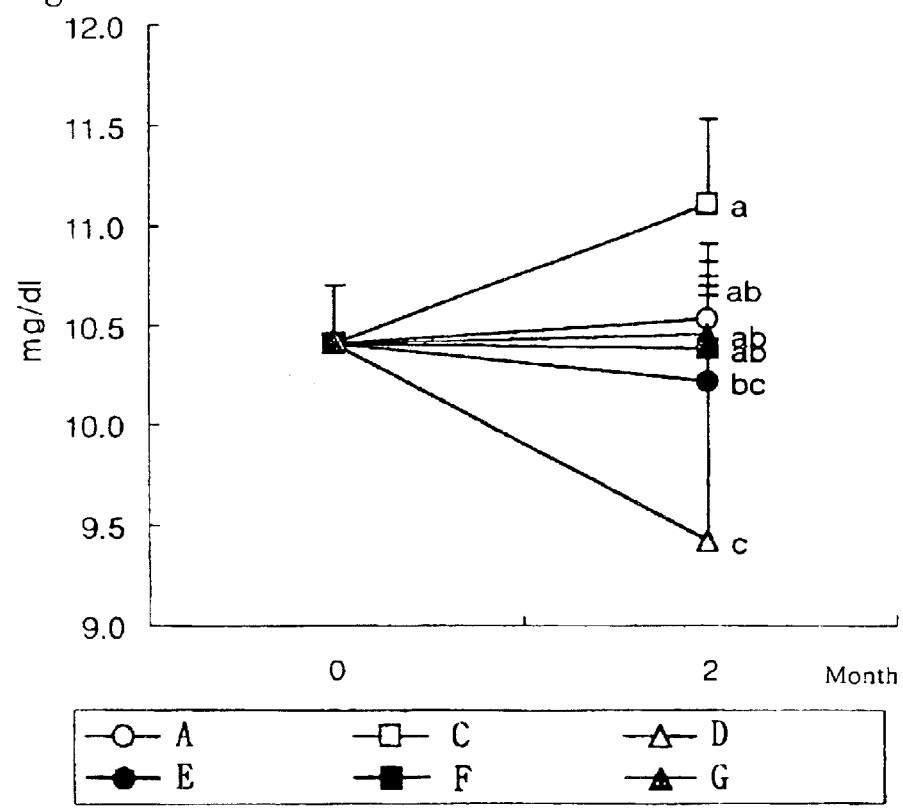
FIG. 3 is a graph that shows the concentration of calcium observed by using Technicon autoanalyzer.
Figure 4:
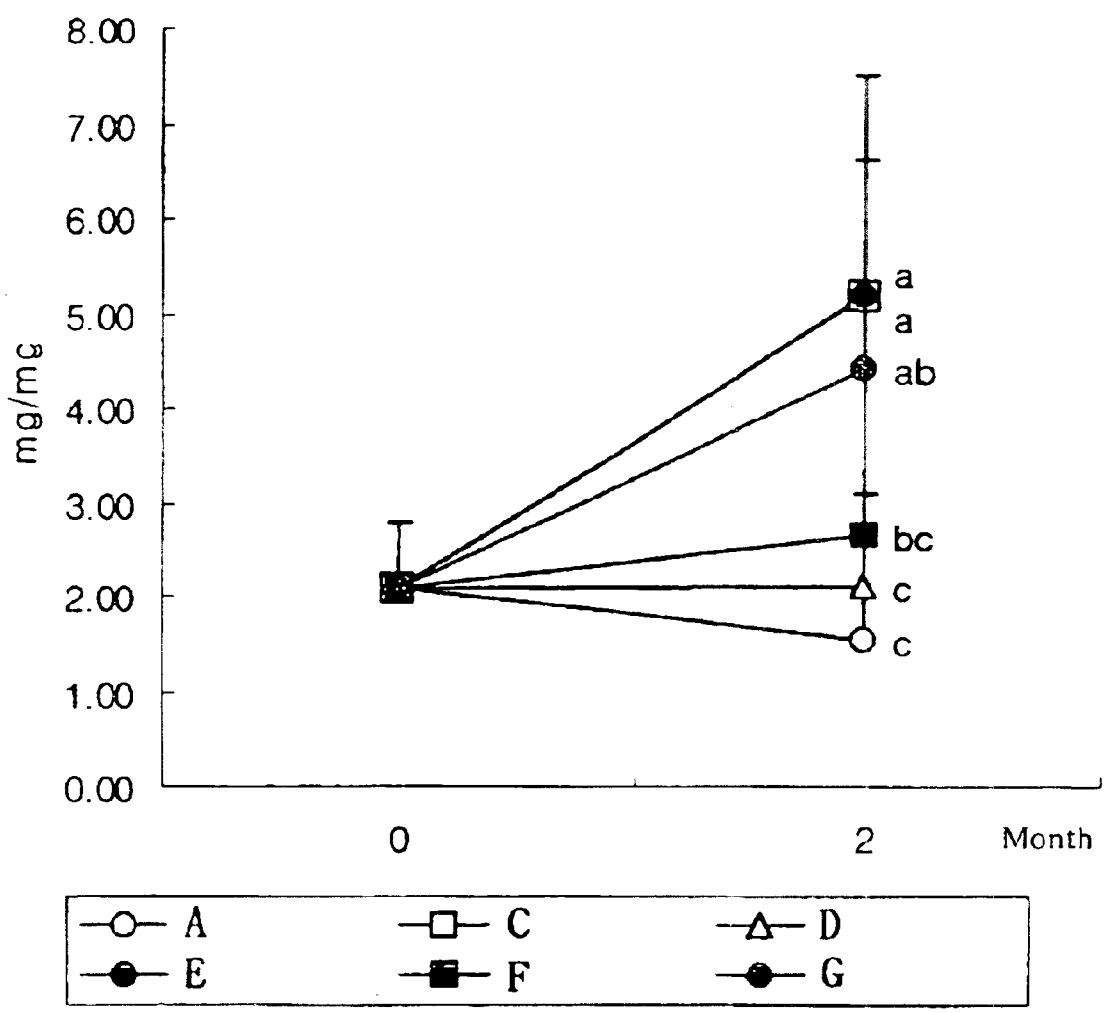
FIG. 4 is a graph that shows the concentration of calcium/creatinine in urine observed by using a calcium kit (Youngdong Pharmaceutical Co., Ltd., Korea).

In order to study the effect of medication on the relationship between the serum calcium concentration and the resulting calcium excretion in urine, the concentration ratio of calcium/creatine of a 24 h urine sample was measured by using a calcium kit (Yeongdong Pharmaceutical Co., Ltd., Korea) and the result is shown in FIG. 4. According to the FIG. 4, the calcium excretion was increased markedly when medicated with calcitriol while there was no difference observed when medicated with alendronate. The amount of calcium excretion increased in groups 1 and 3 with a composite drug containing both calcitriol and alendronate, whereas that of group 2 remained at the level comparable to that of a control group (FIG. 4).

3) Measurement of Bone Remodeling Index

The activity level of serum alkaline phosphatase was measured by using Technicon autoanalyzer and the concentration of osteocalcin was measured by using a kit (OSCA test, Brahams, Berlin, Germany) which uses RIA method.

Figure 5:
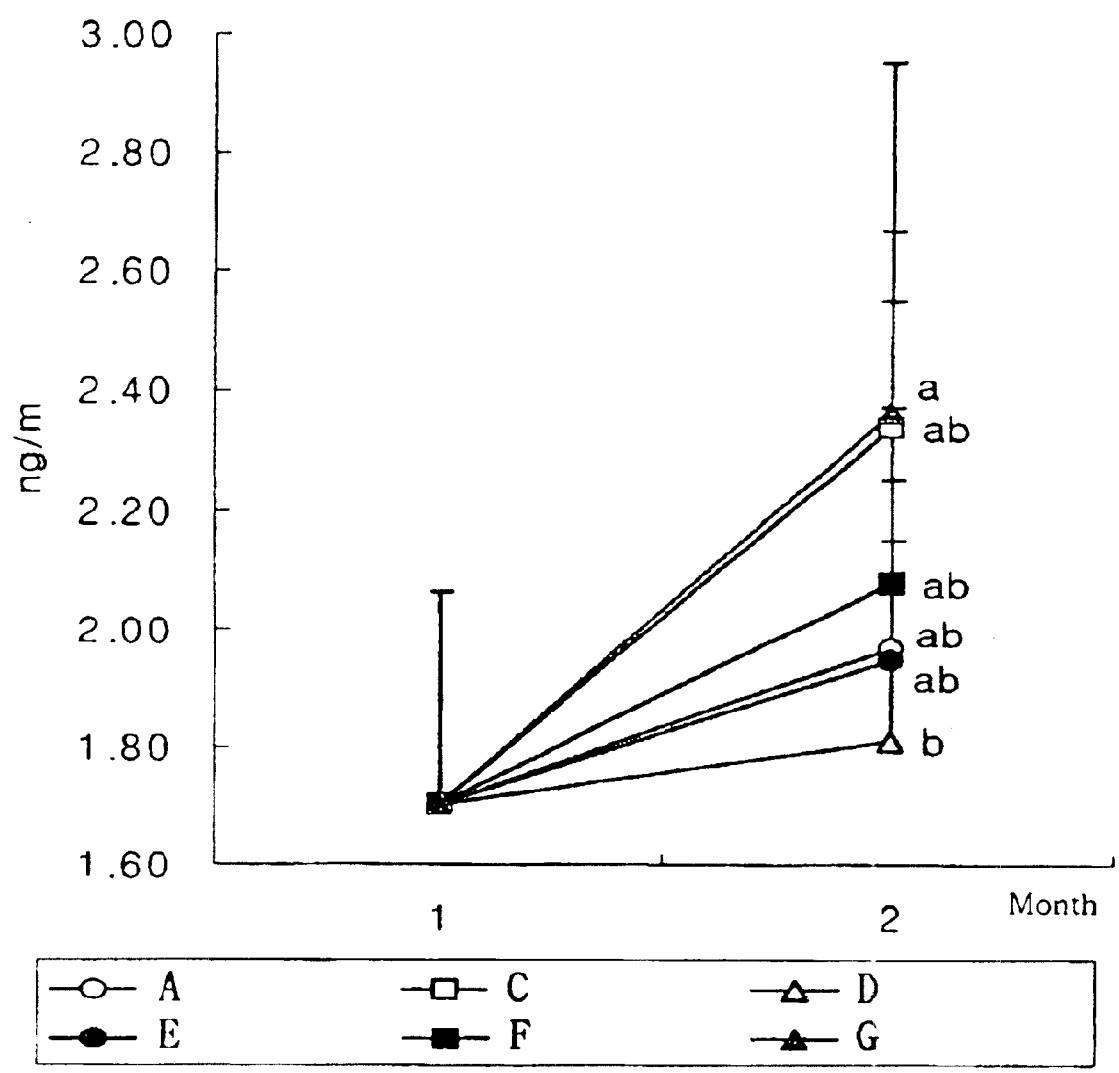
FIG. 5 is a graph that shows the concentration of osteocalcin in serum observed by a kit using RIA method.
Figure 6:
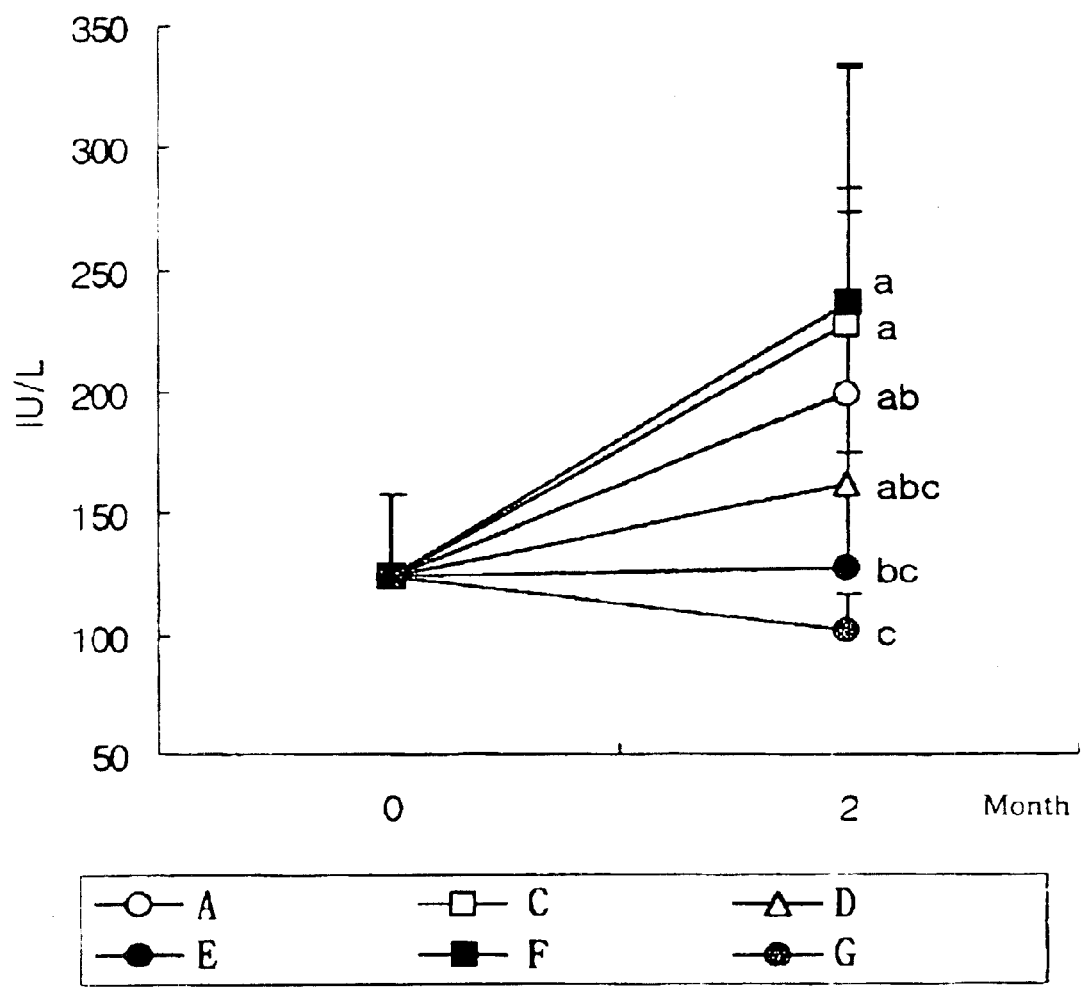
FIG. 6 is a graph that shows the activity of alkaline phosphatase observed by using Technicon autoanalyzer.
Figure 7:
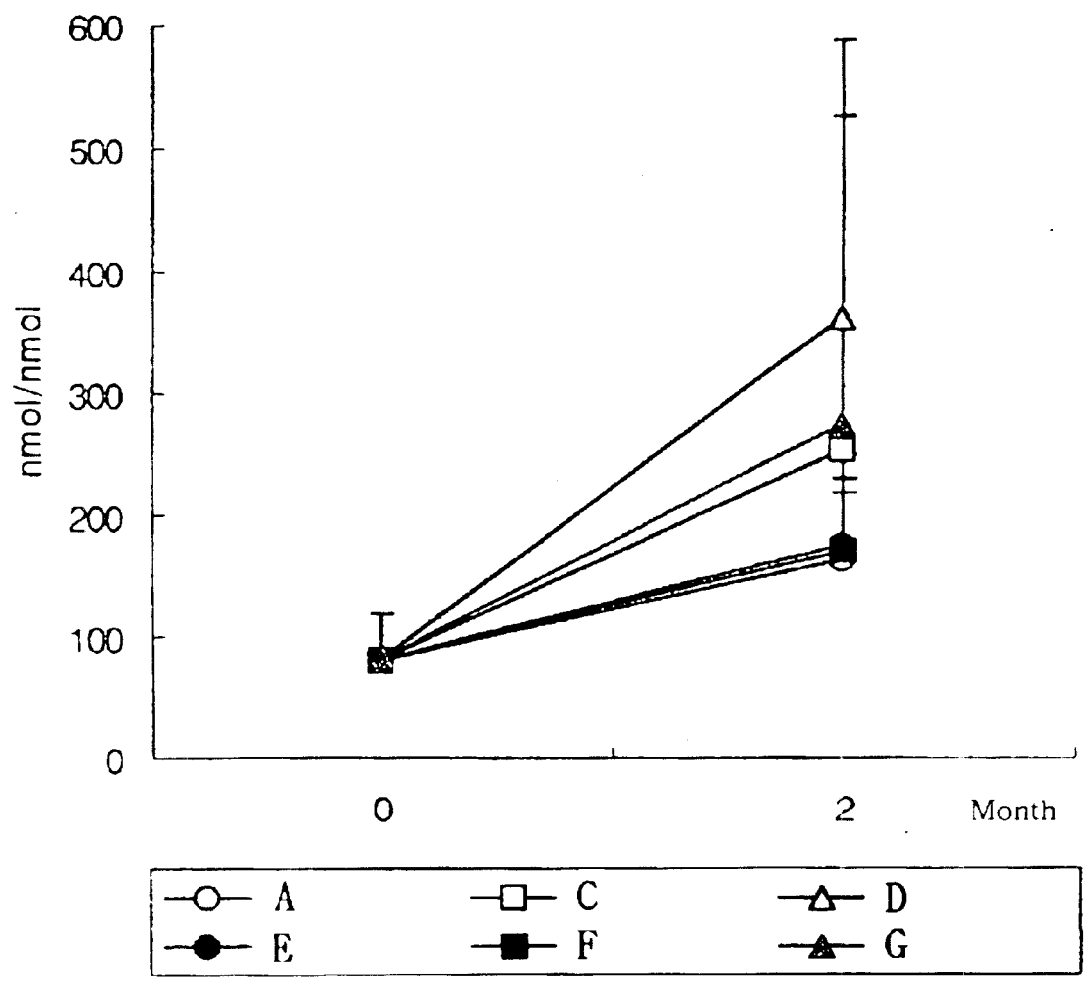
FIG. 7 is a graph that shows the concentration of type I collagen telopeptide (NTx) in urine observed by using Technicon autoanalyzer, which is used as an index for the rate of bone resorption.

As an index of bone remodeling rate, the concentration of serum osteocalcin and the activity of alkaline phosphatase were measured. There was a slight increase in both the concentration of osteocalcin and the activity of alkaline phosphatase when medicated with calcitriol alone while they were decreased when medicated with alendronate, although not to a significant level (FIGS. 5 & 6). There was no change observed in concentration of osteocalcin in all the groups treated with a composite medication. The activity of alkaline phosphatase decreased significantly in the group 3 with a composite medication, however, the groups 1 and 2 did not show any noticeable change in the activity of alkaline phosphatase thus implying that the rate of bone remodeling did not decrease in groups 1 and 2.

4) Measurement of Bone Resorption Index

The ratio of NTx/creatine in urine was calculated by measuring the concentration of N-telopeptide (NTx) of a 24 h urine sample, a by-product of type I collagen, using a kit (Osteomark, Ostex, USA). The result showed that there was no significant change in the rate of bone resorption due to medications (see FIG. 7).

From the above experimental examples 1 and 2, the group 2 with a composite medication (0.1 $\mu$g/kg of calcitriol+1.0 mg/kg of alendronate) was shown to be the most optimal concentration ratio for a composite pharmaceutical preparation because the progress of osteoporosis was effectively prevented without inhibiting the rate of bone remodeling, and also the serum calcium concentration and the calcium excretion in urine were maintained at a normal level. Thus obtained composite pharmaceutical preparations were evaluated for their safety according to the standard acute and subacute toxicity tests described in Korea Food & Drug Administration 9856 issued on Apr. 29, 1998 as in the following experimental examples 3 and 4 and their safety was accordingly confirmed.

Experimental Example 3

Acute Toxicity Test of a Composite Pharmaceutical Agent containing Both Calcitriol and Alendronate The toxicity of a single dose of a composite pharmaceutical agent containing calcitriol and alendronate via oral administration on experimental animals was examined to evaluate the safety of the above composite pharmaceutical agent. In this experiment, the above composite pharmaceutical agent was administered on Sprague-Dawley white rats to study the acute oral toxicity by means of $LD_{50}$, general conditions, body weight and the amount of dietary intake, and was examined further by an autopsy.

Nursing Conditions

One hundred eighty of 45 week old Sprague-Dawley white rats (90 males and 90 females) were raised in a SPF room designed by Techniplast Co. in Italy, located annexed to the animal care center in the Department of Pharmacology of Choong-Ang University in Korea under the conditions of 23±2° C., relative humidity of 60+29%, 13–15 times of air ventilations/h, illumination of 12 h/day (from 7 a.m.–7 p.m.). The above experimental white rats were placed in a cage and allowed to freely intake solid feedstuff (Hanil Feed: Greenpia Co., Ltd., Korea) sterilized by an X-ray irradiation and drinks (heat-sterilized tap water).

Preparation of Sample Reagents

Calcitriol stored in a light-resistant container in a −20° C. freezer was weighed for 1.0 mg and added into a brown flask. 1.0 $\mu$g/mL and 10 $\mu$g/mL solutions were freshly prepared by adding a solvent (100% ethanol: MCT=5:95) when needed, and mixed with a 0.5% CMC-Na aqueous solution, where alendronate monosodium was already suspended.

Determination of the Amount of Medication

The mixing ratio between the amount of medication for calcitriol and alendronate was determined to be 0.5 $\mu$g:5 mg based on the amount administered to humans. Animals were proportionally divided into 8 different groups based on the values of $LD_{50}$ and the total of 9 groups including a control group were determined as shown in the table 2. Medication was orally administered after making the volume totalling 1 mL. Based on the relationship between the human body weight and the amount administered to white rats, the minima doses were set to be 0.2 $\mu$g/kg and 2.0 mg/kg for calcitriol and alendronate, respectively.

TABLE 2

| Group | 1 | 2 | 3 | 4 | 5 | 6 | 7 | 8 | Control |
|---|---|---|---|---|---|---|---|---|---|
| Calcitriol ($\mu$g/kg) | 125 | 100 | 75 | 50 | 25 | 5 | 1 | 0.2 | 0.0 |
| Alendronate (mg/kg) | 1250 | 1000 | 750 | 500 | 250 | 50 | 10 | 2.0 | 0.0 |

Experimental Items

1) Measurement of $LD_{50}$

In order to measure the values of $LD_{50}$ f both male and female white rats, animals under experiment were divided into 8 medication groups and a control group wherein each group consisted of 10 white rats and was orally administered. Then, the number of animals which were dead within two weeks after the medication were counted and their $LD_{50}$ values were calculated by using Brehrens-Karber method.

The resulting $LD_{50}$ of white rats administered with the composite drug containing calcintriol and alendronate are as follows.

The moralities for both male and female white rats, treated with a single oral administration with the composite medication consisting of calcitriol and alendronate (1 $\mu$g/kg: 10 mg/kg), are shown in the following table 3.

TABLE 3

| Oral Administration (calcitriol + alendronate) | | Mortality | |
|---|---|---|---|
| calcitriol($\mu$g/kg) | alendronate(mg/kg) | Female | Male |
| 125 | 1250 | 10/10 | 10/10 |
| 100 | 1000 | 9/10 | 9/10 |
| 75 | 750 | 6/10 | 5/10 |
| 50 | 500 | 0/10 | 0/10 |
| 25 | 250 | 0/10 | 0/10 |
| 5 | 50 | 0/10 | 0/10 |
| 1 | 10 | 0/10 | 0/10 |
| 0.2 | 2.0 | 0/10 | 0/10 |

The values of $LD_{50}$ of the composite drug of calcitriol and alendronate were calculated according to Brehrens-Karber method. The result showed that the $LD_{50}$ of the male rat was 77.5 $\mu$g/kg for calcitriol and 775 mg/kg for alelidronate, whereas that of female rat was 75.0 $\mu$g/kg for calcitriol and 750 mg/kg for alendronate.

2) Observation of Normal State

Observations were made daily for all the white rats under experiment for the duration of 2 weeks in such a manner that each mouse was observed every 30 min for the first 6 hr after the medication and then observed once a day at predetermined time from the second day. The results of observations of white rats at normal state are as follows.

For the first 6 hr after the medication, the group of female white rats medicated with more than $LD_{50}$ showed a peculiar behavior that they scratched their heads using their legs and the behavior turned out to be a symptom due to the esophagogastric stimulation. Then, those white rats showed convulsion and dyspnea within 1 hr from the medication. They showed a decrease in autopathy after 2 hr from the medication, a light degree of behavioral flexibility, maintained lethargic state, and had respiratory stress. Almost all the white rats medicated with not less than 100 µg/kg of calcitriol and 1000 mg/kg of alendronate died within 24 hr of the medication. In the group of white rats medicated with 75 µg/kg of calcitriol and 750 mg/kg of alendronate, 60% of female and 50% of male were dead while in the group medicated with 50 µg/kg of calcitriol and 500 mg/kg of alendronate were all alive. In the group of white rats medicated with 50 µg/kg of calcitriol and 500 mg/kg of alendronate, 3 out of 10 showed the above-mentioned esophagogastric stimulation symptom but they recovered from the symptom on the first day of the convalescence.

3) Measurement of Body weight and Food Intake

All the white rats under experiment were daily measured for their weights and their food intakes at predetermined time before and after each medication for 2 weeks. The results showed that there was no significant change in male and female white rats except those which were dead in food intake as well as in body weight (FIGS. 8–9).

4) Autopsy

Gross findings were obtained from the dead white rats as well as from all the live white rats after killing them by anesthetizing with ether. Abnormal organs or tissues detected by naked eyes were fixed with 10% neutral formalin and then made into standard tissue samples. They were then dyed with hematoxylene and eosin to obtain tissue findings and the results are as follows.

The autopsies of white rats treated with a composite drug containing not less than 75 µg/kg of calcitriol and 750 mg/kg of alendronate showed no abnormal findings except hemostasis of spleen. Autopsies performed for control white rats and those alive at completion of convalescence of 14 days after treating with a composite drug containing calcitriol and alendronate, and there were no abnormal findings except minor hypertrophy of spleen. Tissue autopsies of white rats which were found dead after treating with 100 µg/kg of calcitriol and 1,000 mg/kg of alendronate showed that there were serious hemostasis and hemorrhage of spleen (FIG. 10).

Experimental Example 4

Subacute Toxicity Test of a Composite Pharmaceutical Agent Containing Both Calcitriol and Alendronate Subacute toxicity for a 5 week repetitive dose of a composite pharmaceutical agent containing calcitriol and alendronate via oral administration on experimental white rats was examined to evaluate the safety of the above composite pharmaceutical agent. White rats under experiment were examined once per each day for the duration of 5 weeks of repetitive oral medications and for the duration of 2 weeks of convalescence. In order to evaluate the subacute toxicity of the composite pharmaceutical agent, experiments such as normal state, change in body weight, dietary intake, ophthalmologic examination, acoumetry, urine test, hematological test, hematochemical test, and pathological test were performed after treating with a given medication.

Experimental Animals and Nursing Conditions

Sprague-Dawley white rats were raised under the same condition as described in the acute toxicity test in the Experimental Example 3, with the exception that they were placed into a metabolic cage one day prior to the completion of the experiment. Each experimental group consisted of 20 males and 20 females, and they were treated for 5 weeks. After 2 weeks of convalescence, 10 males and 10 females were selected from each group and were examined.

Preparation of Sample Reagents & Determination of the Amount of Medication

Sample reagents were prepared the same as described in the acute toxicity test in Experimental Example 3. The mixing ratio between the amount of medication for calcitriol and alendronate was determined to be 0.5 µg: 5 mg based on the amount of medication for humans, $LD_{50}$ values already reported, and the amount of medication known to be effective in clinical treatment and prevention of osteoporosis. Five groups were selected via azetropy 5 with 4 different medication groups and a control group as shown in the table 4.

TABLE 4

| Group | 1 | 2 | 3 | 4 | Control |
| --- | --- | --- | --- | --- | --- |
| Calcitriol(µg/kg) | 25 | 5 | 1 | 0.2 | 0.0 |
| Alendronate(mg/kg) | 250 | 50 | 10 | 2.0 | 0.0 |

Experimental Items

1) Mortality Examination

No mortality was observed but both male and female white rats treated with a composite drug containing calcitriol and alendronate were all alive both at the time of completion of medication and at convalescence.

2) Observation of Normal State

Normal state of white rats were observed (a) 3 times per each day during treatment; before medication, immediately after medication, and 2 hr after medication, (b) 2 times per each day during holidays; before medication and immediately after medication, and (c) once per each day during convalescence.

Esophagogastric stimulating symptom and lethargic state were observed up to day 3 after medication but those symptoms disappeared after day 5. All the other experimental groups did not show any particular change in normal state that appears to be due to the medication.

3) Change in Body Weight and Water Intake

Body weight was measured once every 3 days during the medication and through the convalescence. The accumulated amount of water intaken for a period of 7 days was measured once per week and the amount of daily intake per each mouse was estimated from this. The result showed that there was no significant change in body weight (FIG. 11) nor in water intake (FIG. 10) in all the experimental groups treated with the composite pharmaceutical agent containing calcitriol and alendronate until the completion of medication and convalescence.

4) Ophthalmologic Autopsy

Ophthalmologic autopsies were executed for all the white rats under the experiment during the inspection, and on the $5^{th}$ week of the experiment only 5 males and 5 females selected from each group were examined. While observing the external ophthalmologic state atropine was instilated and anterior segment of eye, intermediate transmitting body of eye, and fundus of eye were examined. When there was no change due to a given medication observed by the examination on the 5$^{th}$ week, the subsequent examination at convalescence was omitted. The result showed that there was no significant ophthalmologic change in all the experimental groups treated with the composite pharmaceutical agent of calcitriol and alendronate until the completion of medication and convalescence.

5) Acoumetry

Outreflex was examined on the 5$^{th}$ week of medication by means of a Gaidan-Boizuru machine (about 600 Hz) for 10 males and 10 females from each experimental group. When there was no change due to a given medication observed by the examination on the 5$^{th}$ week, the subsequent examination at convalescence was omitted. The result showed that there was no significant acoumetric change in all the experimental groups treated with the composite pharmaceutical agent of calcitriol and alendronate until the completion of medication and convalescence.

6) Urine Test

On the 5$^{th}$ week of medication and on the 2$^{nd}$ week of convalescence, 10 males and females were selected from each experimental group and were forced to fast but allowed to drink water, and urine samples were collected from them after 4 hr of fasting. Then they were allowed to freely intake both food and water, and urine samples were collected from them after 20 hr of their free diet. The urine samples obtained from the first 4 hr were analyzed with respect to leucocytes, nitrite, urobilinogen, pH, proteins, ketone bodies, urine sugar, occult blood, specific gravity, biliruibn (AMES urine test paper, N-Nultistix SG-L: Japan Bayer, Samkong Co., Ltd.), colors and sediments. Urine samples obtained from 20 hr were used to estimate Na, K and Cl (total quantity measurement). The result showed that there were no significant change in urines obtained from all the experimental groups treated with the composite pharmaceutical agent of calcitriol and alendronate until the completion of medication and convalescence but they all stayed within the normal range.

7) Hematological Examination

White rats were fasted overnight for about 16 hr before killing and they were dissected along the median line after anesthetizing with ether. Blood samples were collected from the abdominal arteries and stored in vacutainers (Bechon Dickinson Vacutainer Systems Europe England) containing anticoagulant (7.5% EDTA-2K). The blood samples were then used to analyze red blood cell (RBC) count (detection of change in electric resistance), amount of hemoglobin (cyanomenohemnoglobin method), hematocrit value (estimate RBC count and mean hematocrit volume), mean corpuscular volume (detection of change in electric resistance), mean corpuscular hemoglobin (estimate from the amount of hemoglobin and hematocrit value), platelet count (detection of change in electric resistance), (Abnormality Automatic Analyzing Instrument Cell-Dyne 3000, Abbot Co.), reticulocyte (Brecher method) and differential white count (May-Giemsa method). Here, blood plasma obtained by centrifugation (10 min at 3,000 rpm) of blood samples treated with 3.8% sodium citrate was used to estimate the above-mentioned tests by means of prothrombin time (Quick method) and the results are as follows.

At Completion of Medication

There was no significant change observed in all the experimental groups treated with the composite pharmaceutical agent of calcitriol and alendronate.

At Completion of Convalescence

There was no significant change observed in all the experimental groups treated with the composite pharmaceutical agent of calcitriol and alendronate.

8) Hematochemical Examination

Blood samples were collected from abdominal veins as in the case with hematological examination and treated with heparin. Blood sera were obtained by centrifugation (10 min at 3,000 rpm) of the blood samples and were used to analyze GPT and GOT (Abnormal UV rate method, Abnormality Automatic Analyzing Instrument, CH16, Texas International INC.), ALP (Bessey-Lowry method), total cholesterol (CEH-COD-POD method), total bilirubin, blood glucose (hexokinase PD method), urea-nitrogen (UreaGL PC method), inorganic phosphorous (molybdic acid method) and total protein (Biuret method) (Abnormal UV rate method, Abnormality Automatic Analyzing Instrument, Monach, Instrumentation Laboratory). Reagents used in the above examinations were purchased from Stanbio Laboratory Inc. (Texas, USA) and the results are as follows.

At Completion of Medication

There was a little increase in GPT activity in male white rats treated with 25 µg/kg of calcitriol and 250 mg/kg of alendronate, and those treated with 5 µg/kg of calcitriol and 50 mg/kg of alendronate. GFP activity was increased in all the experimental white rats. However, there was no significant dosage-dependent change and the level of GTP activity was relatively high even in a control group treated with solvent thus implying that the little increase in GTP activity was due to a light hematolysis incurred while collecting blood samples. The level of blood glucose was increased a little in all the male and female experimental white rats, however, there was no significant dependency observed on the volume. There was a little increase in a control group treated with solvent and urinal glucose was not detected in urines thus suggesting that the little increase in the level of glucose was not due to diabetes but a temporary increase due to a stress. Therefore, it can be concluded from the above results that there was no significant dosage-dependent change in both experimental groups and a control group due to medications with the exceptions of a little increase in GOT activity and glucose level.

At Completion of Convalescence

The GPT activity in male white rats became normal at completion of convalescence treated with 25 µg/kg of calcitriol and 250 mg/kg of alendronate, and those treated with 5 µg/kg of calcitriol and 50 mg/kg of alendronate. GOT activity became lower in all the experimental groups as compared to that at completion of medication. However, there was no significant dosage-dependent change and the level of GTP activity was relatively high even in a control group treated with solvent thus implying that the little increase in GTP activity was due to a light hematolysis incurred while collecting blood samples. Therefore, it can be concluded from the above results that there was no significant dosage-dependent change in both experimental groups and a control group due to medications with the exceptions of a little increase in GOT activity and glucose level as is the case with at completion of medication.

9) Autopsy

Gross findings were obtained from the dead white rats as well as from all the live white rats after killing them by anesthesizing with ether. Abnormal organs or tissues detected by naked eyes were fixed with 10% neutral formalin and then made into standard tissue samples. They were then dyed with hematoxylene to obtain tissue finding and the results are as follows.

At Completion of Medication

The autopsies of white rats treated with a composite medication of 25 µg/kg of calcitriol and 250 mg/kg of alendronate showed a significant level of hypertrophy of spleen but there were no abnormal findings in white rats treated with less than the above-mentioned dosage. There were no tissue findings that showed significant changes due to medication other than spleen.

At Completion of Convalescence

The autopsies of white rats treated with a composite medication of 25 µg/kg of calcitriol and 250 mg/kg of alendronate showed a significant level of hypertrophy of spleen but there were no abnormal findings in white rats treated with less than the above-mentioned dosage. There were no tissue findings that showed significant changes due to medication other than spleen.

10) Pathological Examination

Upon collecting blood samples all the experimental white rats were killed by exsanguinations. After observing the abnormalities of all the organs by naked eyes, brains, hypothalamus, thyroid gland including parathyroid, salivary gland (glandular submaxillaris and glandular subligualis), thymus, heart, lungs including bronchi, liver, spleen, kidney, testicle, adrenal gland, ovary, prostate gland, seminal veside, uterus, and sternum were ablated and weighed, respectively. The experimental white rats were fasted on the day of autopsy and the relative weight of each organ mentioned above was estimated to 100 g of body weight, respectively. Also, abnormal regions of spinal cord, nervus ishiadicus, thoracic aorta, trachea, tongue, esophagus, stomach, duodenum, jejunum, ileum, cecum, colon, rectum, pancreas, and mesenterium were ablated and fixed with 10% formaline with phosphate buffer, and brains and spinal cords (sternum and femur) were fixed with Bouin's solution and embedded with paraffin. Specimens of all the tissues and organs obtained from the white rats during medication and convalescence all the experimental groups and the solvent control group were dyed with hematoxylene and eosin (H & E) and observed under a microscope. The results showed no apparent changes due to medication Conclusion from the Experimental Examples 3–4

Male and female Sprague-Dawley white rats were orally administered with a composite drug containing both calcitriol and alendronate with a mixing ratio of 1:10,000 either once or repeatedly for the duration of 5 weeks for the tests of acute and subacute toxicities and the results were as follows.

First, the results of acute toxicity test for the above composite medication are as follows.

The values of $LD_{50}$ for the oral medication of the composite drug of calcitriol and alendronate were calculated by using Brehrens-Karber method. The result showed that the $LD_{50}$ of the male white rats was 77.5 µg/kg for calcitriol and 775 mg/kg for alendronate, whereas that of female white rats was 75.0 µg/kg for calcitriol and 750 mg/kg for alendronate, respectively. All the experimental white rats were alive when treated once orally with the composite medication of 50 µg/kg of calcitriol and 500 mg/kg of alendronate and there were no abnormalities observed in normal state except esophagogastric stimulating symptom and lethargy. Body weight, the amount of dietary intake and the result of urine test were all shown to be normal.

The autopsies of white rats killed by the oral treatment of the composite drug of not less than 75 µg/kg of calcitriol and not less than 750 mg/kg of alendronate revealed that there were serious hemostasis and hemorrhage of spleen, however, no other particular lesions were observed due to the medication.

Second, the results of subacute toxicity test for the above composite medication are as follows.

At completion of Repetitive Medication

All the experimental white rats were alive after repetitive oral treatment for 5 weeks with the composite medication of 25 µg/kg of calcitriol and 250 mg/kg of alendronate and there were no abnormalities observed in normal state, the amount of dietary intake, ophthalmological examination, acoumetric examination, hematological examination and hematochemical examination.

The autopsies of the above white rats revealed that there were no abnormal findings in the weight of each organ except hypertrophy of spleen, however, there were also observed moderate level of local lung septum and slight hemostasis in spleen, liver, kidney, and esophagogastric mucosal edema and extravasation of inflammatory cells. However, these lesions were also observed in an experimental group treated with a low dosage of composite medication of less than 5 µg/kg of calcitriol and less than 50 mg/kg of alendronate as well as in a control group and thus these lesions were not considered due to the medication. There were no abnormal findings in the brain, bone marrow, sexual gland and peptic gland.

At Completion of Convalescence

Experimental white rats at completion of convalescence of 2 weeks after repetitive oral administration with composite drug of 25 µg/kg of calcitriol and 250 mg/kg of alendronate for 5 weeks were all alive and there were no abnormalities observed in normal state, the amount of dietary intake, ophthalmological examination, acoumetric examination, hematological examination and hematochemical examination.

The autopsies of the above white rats revealed that there were no abnormal findings in the weight of each organ except hypertrophy of spleen, however, there were also observed moderate level of local lung septum and slight hemostasis in spleen, liver, kidney, and esophagogastric mucosal edema and extravasation of inflammatory cells. However, these lesions were also observed in an experimental group treated with a low dosage of composite medication of less than 5 µg/kg of calcitriol and less than 50 mg/kg of alendronate as well as in a control group and thus these lesions were not considered due to the medication. A slight esophagogastric inflammation observed appears not a peculiar change but is considered as a reversible injury in rodents in evaluating the toxicity of a given medication. There were no abnormal findings in brain, bone marrow, sexual gland and peptic gland.

As mentioned above, the single oral administration of a composite drug of calcitriol and alendronate with a mixing ratio of 1:10,000 showed that the $LD_{50}$ was shown to be more than 75 µg/kg and 750 mg/kg for calcitriol and alendronate, respectively, thus proving that this is a low toxic drug. The repetitive oral administration for 5 weeks of a composite drug containing 25 µg/kg of calcitriol and 250 mg/kg of alendronate also did not incur any noticeable subacute toxicity at completion of convalescence as well as at completion of administration, and considering that the supposed human dosage (based on 60 kg of average body weight of a person) is only equivalent to one $3000^{th}$ of that administered in white rats (i.e., 0.5 µg of calcitriol and 5 mg of alendronate) the composite drug containing calcitriol and alendronate according to the present invention is thus thought to be safe.

Experimental Example 5

Tests of a Composite Drug Containing Calcitriol and Alendronate for the Various Mixing Ratios Between Calcitriol and Alendronate 1) The miscibility between a mixture of calcitriol and alendronate and additives such as an excipient Excipients were added to the above mixture of calcitriol and alendronate (5 μg: 50 mg) in a certain ratio as shown in the following tables 5 and 6.

2) To the resulting mixture in 1) was then added 5% of water content and stored it at 40° C. for 14 days.

The stability of the above mixture was examined by means of HPLC (high performance liquid chromatography) and the results are shown in the following tables 5 and 6.

TABLE 5

Stability of calcitriol (residual rate %)

| Classification | Mixing Ratio | Dry | Water content (%) |
|---|---|---|---|
| Calcitriol + Alendronate | — | 80.1 | 79.6 |
| Mannitol | 9:1 | 101.9 | 101.6 |
| White sugar | 9:1 | 94.7 | 95.0 |
| Cellactose | 9:1 | 64.5 | 63.5 |
| β-cyclodextrin | 9:1 | 97.5 | 96.3 |
| Povidone | 9:1 | 98.3 | 99.1 |
| Hydroxypropyl methyl cellulose | 3.6:1 | 95.4 | 93.5 |
| Hydroxypropyl cellulose | 3.6:1 | 91.8 | 92.2 |
| Sodium lauryl sulfate | 3.6:1 | 83.9 | 83.4 |
| Low substituted Hydroxymethyl cellulose | 3.6:1 | 95.4 | 94.3 |
| Croscarmellose sodium | 3.6:1 | 93.5 | 92.0 |
| Calcium carboxy methyl cellulose | 3.6:1 | 75.2 | 73.5 |
| Crospovidone | 3.6:1 | 88.5 | 89.7 |
| Butylated hydroxytoluene | 3.6:1 | 27.7 | 14.4 |
| Butylated hydroxyanisole | 3.6:1 | 84.6 | 78.3 |
| DL-α-tocopherol | 3.6:1 | 86.4 | 86.2 |
| Calcium stearate | 3.6:1 | 101.7 | 101.1 |
| Magnesium stearate | 3.6:1 | 100.3 | 98.9 |
| Colloidal Silicon dioxide | 3.6:1 | 99.8 | 98.5 |

TABLE 6

Stability of Alendronate (residual rate %)

| Classification | Mixing Ratio | Dry | Water content (%) |
|---|---|---|---|
| Calcitriol + Alendronate | — | 99.0 | 100.2 |
| Mannitol | 1:1 | 96.2 | 99.3 |
| White sugar | 1:1 | 100.8 | 97.8 |
| Cellactose | 1:1 | 95.4 | 97.3 |
| β-cyclodextrin | 1:1 | 100.2 | 98.4 |
| Povidone | 1:1 | 97.7 | 99.9 |
| Hydroxypropyl methyl cellulose | 1:1 | 98.2 | 96.1 |
| Hydroxypropyl cellulose | 1:1 | 75.7 | 85.2 |
| Sodium lauryl sulfate | 5:2 | 100.4 | 99.7 |
| Low substituted Hydroxymethyl cellulose | 5:2 | 98.1 | 98.7 |
| Croscarmellose sodium | 5:2 | 100.0 | 97.4 |
| Calcium carboxy methyl cellulose | 5:2 | 98.0 | 97.1 |
| Crospovidone | 5:2 | 100.2 | 97.6 |
| Butylated hydroxytoluene | 5:2 | 100.6 | 99.1 |
| Butylated hydroxyanisole | 5:2 | 97.9 | 97.2 |
| DL-α-tocopherol | 5:2 | 94.2 | 99.0 |
| Calcium stearate | 5:2 | 95.4 | 98.3 |
| Magnesium stearate | 5:2 | 97.7 | 98.4 |
| Colloidal Silicon dioxide | 5:2 | 99.0 | 100.1 |

The results of the above tables 5 and 6 showed that mannitol as an excipient, porvidone as a binder, calcium stearate or magnesium stearate as a lubricant are having an excellent property in its designated field, respectively. Butylated hydroxytoluene and butylated hydroxyanisole as antioxidants were thought to affect the stability of calcitriol at first, however, additional experiments confirmed that they only affect calctriol at the level of its analysis and considering that they are used only trace amount it would not incur any problem. As a result, additives being incorporated into the pharmaceutical agent were selected as follows: mannitol as an excipient, porvidone as a binder, calcium stearate as a lubricant, butylated hydroxytoluene and butylated hydroxyanisole as antioxidants, and lauryl sodium sulfate as a resorption fortifier.

PREPARATIVE EXAMPLE

The pharmaceutical agents according to the present invention were prepared in the form of naked tablets, enteric coated tablets, granules, enteric coated granules, capsules, enteric coated capsules.

Preparative Examples 1–3

Preparation of Naked Tablets

Naked tablets were prepared according to the composition and the contents shown in the following table 7.

First, D-mannitol was added to a mixture consisting of calcitriol and ethanol, and were then added ethanol, antioxidants and a binder.

Apart from the process of preparing calcitriol, other ingredients of alendronate, mannitol, resorption fortifier were mixed, and then ethanol and a binder were added to it. Then, calcitriol and alendronate were mixed and a disintegrating agent and a lubricant were added and thus tableted.

TABLE 7

| | Classification | Preparation Examples (mg) | | |
|---|---|---|---|---|
| | | 1 | 2 | 3 |
| Main Ingredients | Alendronate | 6.53 | 6.53 | 6.53 |
| | Calcitriol | 0.0005 | 0.0005 | 0.0005 |
| Excipient | D-mannitol | 103.23 | 102.78 | 37.23 |
| Antioxidant | Butylated hydroxytoluene | 0.12 | 0.12 | 0.12 |
| | Butylated hydroxyanisole | 0.12 | 0.12 | 0.12 |
| Binder | Povidone | 3 | 3 | 3 |
| Solvent | Ethanol | adequate | adequate | adequate |
| Sustained-releasing agent | Hydroxypropyl methyl cellulose | — | — | 24 |
| | Methyl cellulose | — | — | 48 |

TABLE 7-continued

| Classification | | Preparation Examples (mg) | | |
|---|---|---|---|---|
| | | 1 | 2 | 3 |
| Disintegrating agent | Croscarmellose sodium | 6 | 6 | — |
| Resorption fortifier | Sodium lauryl sulfate | — | 0.45 | — |
| Lubricant | Calcium stearate | 1 | 1 | 1 |

Preparative Examples 4–6

Preparation of Enteric Coated Tablets

Enteric coated tablets were prepared the same as in the preparation of the above preparation examples 1–3 with the exception that the naked tablets prepared in the preparation examples 1–3 were coated with enteric coating solution to have the ingredients and the contents as shown in the following table 8.

TABLE 8

| Classification | | Preparation Examples (mg) | | |
|---|---|---|---|---|
| | | 4 | 5 | 6 |
| Main Ingredients | Alendronate | 6.53 | 6.53 | 6.53 |
| | Calcitriol | 0.0005 | 0.0005 | 0.0005 |
| Excipient | D-mannitol | 103.23 | 102.78 | 37.23 |
| Antioxidant | Butylated hydroxytoluene | 0.12 | 0.12 | 0.12 |
| | Butylated hydroxyanisole | 0.12 | 0.12 | 0.12 |
| Binder | Povidone | 3 | 3 | 3 |
| Solvent | Ethanol | adequate | adequate | adequate |
| Sustained-releasing agent | Hydroxypropyl methyl cellulose | — | — | 24 |
| | Methyl cellulose | — | — | 48 |
| Disintegrating agent | Croscarmellose sodium | 6 | 6 | — |
| Resorption fortifier | Sodium lauryl sulfate | — | 0.45 | — |
| Lubricant | Calcium stearate | 1 | 1 | 1 |
| Enteric coating agent | Hydroxypropyl methyl cellulose phthalate | 9.5 | 9.5 | 9.5 |
| Platicizer | Triethyl citrate | 0.5 | 0.5 | 0.5 |

Preparative Examples 7–9

Preparation of Granules

Granules were prepared as shown in the following table 9.

First, D-mannitol was added to a mixture consisting of calcitriol and ethanol, and was then added with ethanol, antioxidants and a binder. The entire mixture was then pulverized by using a conventional pulverizer into a size of 1435 mesh and then dried at 40° C. to obtain calcitriol granules.

Apart from the process of preparing calcitriol, other ingredients of alendronate, mannitol, resorption fortifier were mixed, ethanol and a binder were again added to the above mixture, and then pulverized by using a conventional pulverizer into a size of 1435 mesh and dried at 40° C. to obtain alendronate granules. Then, calcitriol granules and alendronate granules were mixed, and a disintegrating agent and a lubricant were added and thus tableted.

TABLE 9

| Classification | | Preparation Examples (mg) | | |
|---|---|---|---|---|
| | | 7 | 8 | 9 |
| Main Ingredients | Alendronate | 6.53 | 6.53 | 6.53 |
| | Calcitriol | 0.0005 | 0.0005 | 0.0005 |
| Excipient | D-mannitol | 961.47 | 961.02 | 361.47 |
| Antioxidant | Butylated hydroxytoluene | 1 | 1 | 1 |
| | Butylated hydroxyanisole | 1 | 1 | 1 |
| Binder | Povidone | 25 | 25 | 25 |
| Solvent | Ethanol | adequate | adequate | adequate |
| Sustained-releasing agent | Hydroxypropyl methyl cellulose | — | — | 200 |
| | Methyl cellulose | — | — | 400 |
| Resorption fortifier | Sodium lauryl sulfate | — | 0.45 | — |
| Lubricant | Calcium stearate | 5 | 5 | 5 |

Preparative Examples 10–12

Preparation of Enteric Coated Granules

Enteric coated granules were prepared the same as in the above preparation examples 7–9 with the exception that the granules prepared in the above preparation examples 7–9 were coated with enteric coating solution to have the ingredients and the contents as shown in the following table 10.

TABLE 10

| Classification | | Preparation Examples (mg) | | |
|---|---|---|---|---|
| | | 10 | 11 | 12 |
| Main Ingredients | Alendronate | 6.53 | 6.53 | 6.53 |
| | Calcitriol | 0.0005 | 0.0005 | 0.0005 |
| Excipient | D-mannitol | 751.87 | 751.42 | 271.87 |
| Antioxidant | Butylated hydroxytoluene | 0.8 | 0.8 | 0.8 |
| | Butylated hydroxyanisole | 0.8 | 0.8 | 0.8 |
| Binder | Povidone | 40 | 40 | 40 |
| Solvent | Ethanol | adequate | adequate | adequate |
| Sustained-releasing agent | Hydroxypropyl methyl cellulose | — | — | 160 |
| | Methyl cellulose | — | — | 320 |
| Resorption fortifier | Sodium lauryl sulfate | — | 0.45 | — |
| Enteric coating agent | Hydroxypropyl methyl cellulose phthalate | 146.4 | 146.4 | 146.4 |
| Platicizer | Fatty acid glyceride | 24.4 | 24.4 | 24.4 |
| Lubricant | Talc | 29.2 | 29.2 | 29.2 |

Preparative Examples 13–15

Preparation of Capsules

Capsules were prepared as shown in the following table 11.

First, D-mannitol was added to a mixture consisting of calcitriol and ethanol, and were then added with ethanol, antioxidants and a binder. The entire mixture was then pulverized by using a conventional pulverizer into a size of 1435 mesh and then dried at 40° C. to obtain calcitriol granules.

Apart from the process of preparing calcitriol, other ingredients of alendronate, mannitol, resorption fortifier were mixed, ethanol and a binder were again added to the above mixture and then pulverized by using a conventional pulverizer into a size of 14–35 mesh and dried at 40° C. to obtain alendronate granules. Then, calcitriol granules and alendronate granules were mixed, and a disintegrating agent and a lubricant were added and finally filled into capsules.

TABLE 11

| Classification | | Preparation Examples (mg) | | |
|---|---|---|---|---|
| | | 13 | 14 | 15 |
| Main Ingredients | Alendronate | 6.53 | 6.53 | 6.53 |
| | Calcitriol | 0.0005 | 0.0005 | 0.0005 |
| Excipient | D-mannitol | 182.07 | 181.62 | 67.07 |
| Antioxidant | Butylated hydroxytoluene | 0.2 | 0.2 | 0.2 |
| | Butylated hydroxyanisole | 0.2 | 0.2 | 0.2 |
| Binder | Povidone | 5 | 5 | 5 |
| Solvent | Ethanol | adequate | adequate | adequate |
| Sustained-releasing agent | Hydroxypropyl methyl cellulose | — | — | 40 |
| | Methyl cellulose | — | — | 80 |
| Disintegrating agent | Croscarmellose sodium | 5 | 5 | — |
| Resorption fortifier | Sodium lauryl sulfate | — | 0.45 | — |
| Lubricant | Calcium stearate | 1 | 1 | 1 |
| Capsule | Empty capsule #2[1)] | 64 | 64 | 64 |

[1)]Product of SEOHEUNG Capsule Co., Ltd. (Korea)

Preparative Examples 16–18

Preparation of Enteric Coated Capsules

Enteric coated granules were prepared the same as in the above preparation examples 13–15 with the exception that the ingredients were coated with enteric coating solution and then finally filled into capsules with the ingredients and the contents as shown in the following table 12.

TABLE 12

| Classification | | Preparation Examples (mg) | | |
|---|---|---|---|---|
| | | 16 | 17 | 18 |
| Main Ingredients | Alendronate | 6.53 | 6.53 | 6.53 |
| | Calcitriol | 0.0005 | 0.0005 | 0.0005 |
| Excipient | D-mannitol | 178.07 | 177.62 | 63.07 |
| Antioxidant | Butylated hydroxytoluene | 0.2 | 0.2 | 0.2 |
| | Butylated hydroxyanisole | 0.2 | 0.2 | 0.2 |
| Binder | Povidone | 10 | 10 | 10 |
| Solvent | Ethanol | adequate | adequate | adequate |
| Sustained-releasing agent | Hydroxypropyl methyl cellulose | — | — | 40 |
| | Methyl cellulose | — | — | 80 |

TABLE 12-continued

| Classification | | Preparation Examples (mg) | | |
|---|---|---|---|---|
| | | 16 | 17 | 18 |
| Disintegrating agent | Croscarmellose sodium | 5 | 5 | — |
| Resorption fortifier | Sodium lauryl sulfate | — | 0.45 | — |
| Enteric coating agent | Hydroxypropyl methyl cellulose phthalate | 36.6 | 36.6 | 36.6 |
| Platicizer | Fatty acid glyceride | 6.1 | 6.1 | 6.1 |
| Lubricant | Talc | 7.3 | 7.3 | 7.3 |
| Capsule | Empty capsule #1[2)] | 77 | 77 | 77 |

[2)]Product of SEOHEUNG Capsule Co., Ltd. (Korea)

Experimental Example 6

Stability Test of Enteric Coated Tablets

Enteric coated tablets prepared according to the preparation example 5 were stored for two months under an accelerated condition (40° C., relative humidity 75%) and were examined for the stability of tablets three times and the result is in the following table 13.

In evaluating the stability of tablets, the property was evaluated by observing by naked eyes and was confirmed by means of HPLC. The contents of both calcitriol and alendronate were also measured by HPLC.

TABLE 13

| | First Trial | | Second Trial | | Third Trial | |
|---|---|---|---|---|---|---|
| Test Items | Initial | After two month | Initial | After two month | Initial | After two month |
| Description | White, round-shaped film coated tablet | White, round-shaped film coated tablet | White, round-shaped film coated tablet | White, round-shaped film coated tablet | White, round-shaped film coated tablet | White, round-shaped film coated tablet |
| Identification | positive | positive | positive | positive | positive | positive |
| Calcitriol Content (%) | 109.6 | 109.5 | 110.8 | 109.1 | 109.8 | 109.8 |
| Alendronate Content (%) | 99.8 | 98.9 | 100.3 | 99.3 | 100.0 | 99.8 |

The results shown in the above table 13 revealed that the tablets were stable with the stability test for 2 months both at room temperature and under an accelerated condition.

What is claimed is:

1. A pharmaceutical composition for treatment of metabolic bone disease, which comprises a mixture of first granules and second granules wherein said first granules comprise an effective amount of calcitriol, as an active ingredient, and at least one excipient, and said second granules comprise an effective amount of alendronate, as an active ingredient, and at least one excipient; and wherein said composition contains about 1,000–50,000 parts by weight of alendronate per one part by weight of calcitriol; and further wherein said excipient in both granules comprises mannitol, said mannitol comprising about 70 to 98 weight % of the total composition, and wherein about 50–60 weight percent of the total mannitol is combined with said calcitriol, and about 40–60 weight percent of the total mannitol is combined with said alendronate.

2. The pharmaceutical composition of claim 1, wherein said composition is in a form of uncoated tablets, enteric coated tablets, enteric coated granules, capsules or enteric coated capsules.

3. The pharmaceutical composition of claim 1, further comprising, as a resorption fortifier, an additive comprising about 0.01 to 10 weight percent of sodium lauryl sulfate based on the weight of the total composition.

4. The pharmaceutical composition of claim 1, wherein at least one of said granules further comprises ethanol.

5. The pharmaceutical composition of claim 1, which is enteric coated granules.

6. The pharmaceutical composition of claim 1, wherein said mannitol is D-mannitol.

7. The pharmaceutical composition of claim 1, which further calcium stearate in an amount of 0.1 to 20% wt. % based on the total composition.

8. The pharmaceutical composition of claim 1, which further comprises magnesium stearate in an amount of 0.1 to 20 wt. % based on the total composition.

9. The pharmaceutical composition of claim 1, wherein said mannitol and said calcitriol and alendronate, have a mixing ratio of mannitol: (calcitriol+alendronate) of 9:1.

10. The pharmaceutical composition of claim 1, which further comprises a sustained-release additive selected from the group consisting of hydroxypropyl methyl cellulose, methyl cellulose, hydroxypropyl cellulose and ethyl cellulose.

11. The pharmaceutical composition of claim 1, which further comprises butylated hydroxytoluene or butylated hydroxyanisole.

12. The pharmaceutical composition of claim 1, which further comprises povidone, calcium stearate, butylated hydroxytoluene, butylated hydroxyanisole and sodium lauryl sulfate.

13. A method of treating metabolic bone disease which comprises administering an effective amount of the pharmaceutical composition of claim 1 to a mammal in need thereof.

14. The method of claim 13, wherein said metabolic bone disease comprises osteoporosis, Paget's Disease, rachitis, osteomalacia, renal osteodystrophy, hyperparathyroidism and hypoparathyroidism.

15. The method of claim 13, wherein said mammal is a human.

16. The method of claim 13, wherein said metabolic disease is osteoporosis.

* * * * *